United States Patent [19]

Schohe et al.

[11] Patent Number: 5,463,105
[45] Date of Patent: Oct. 31, 1995

[54] SUBSTITUTED BASIC 2-AMINOTETRALIN IN PHARMACEUTICALS

[75] Inventors: Rudolf Schohe, Wuppertal; Thomas Glaser, Röesrath; Jörg Traber, Lohmar, all of Germany; George S. Allen, Nashville, Tenn.

[73] Assignee: Bayer Aktiengesellschaft, Leverkusen, Germany

[21] Appl. No.: 131,267

[22] Filed: Oct. 1, 1993

Related U.S. Application Data

[62] Division of Ser. No. 891,485, May 29, 1992, Pat. No. 5,298,513.

[30] Foreign Application Priority Data

Dec. 10, 1986 [DE] Germany ............ 36 42 192.8
Jun. 1, 1987 [DE] Germany ............ 37 18 317.6

[51] Int. Cl.$^6$ .......................................... C07C 271/08
[52] U.S. Cl. ............................................... 560/29
[58] Field of Search ........................ 560/29; 514/542

[56] References Cited

U.S. PATENT DOCUMENTS

| 4,018,773 | 4/1977 | Condon et al. |
| 4,081,444 | 3/1978 | Condon et al. |
| 4,239,903 | 12/1980 | Isoda et al. |
| 4,410,519 | 10/1983 | Seiler et al. ............ 424/226 |
| 4,465,055 | 8/1984 | Mercatoris et al. |
| 4,748,182 | 5/1988 | Hibert et al. |
| 4,789,676 | 12/1988 | Hibert et al. |
| 4,798,914 | 1/1989 | Link et al. |
| 4,857,526 | 8/1989 | Hibert et al. |
| 4,876,284 | 10/1989 | Arvidsson et al. |
| 4,880,802 | 11/1989 | Schohe et al. |
| 4,920,118 | 4/1990 | Hilbert et al. |
| 4,954,500 | 9/1990 | Hibert et al. |

FOREIGN PATENT DOCUMENTS 0041488 5/1981 European Pat. Off.

OTHER PUBLICATIONS

M. B. Emerit, *European Journal of Pharmacology*, 127, 1986, pp. 67–891.
M. B. Emerit, *Biochemical Pharmacology*, vol. 34, 1985, pp. 883–892.
Chemical Abstracts, vol. 106, 1987, p. 94.
Robins and Walker, *J. Chem. Soc.*, "A New and Specific Aromatisation Reaction. Part III Aromatisation 1:4–Dioxocyclohexane Rings," 1958, pp. 409–421.
John W. Cornforth, *J. Chem. Soc.*, 1942, pp. 689–691.
Theodora W. Greene, *Protective Groups in Organic Synthesis*, 1981, p. 89.
W. Clark Still, *J. Org. Chem.*, 1978, pp. 2923–2925.
W. Clart Still, *Aldrichimica Acta*, vol. 18, 1985, p. 25.

*Primary Examiner*—José G. Dees
*Assistant Examiner*—Samuel Barts
*Attorney, Agent, or Firm*—William C. Gerstenzang; Sprung Horn Kramer & Woods

[57] ABSTRACT

For treatment of disorders of the central nervous system, the cardiovascular system or the intestinal tract, the new substituted basic 2-aminotetralins of the formula

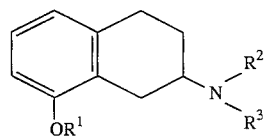

in which
$R^1$ represents hydrogen or alkyl,
$R^2$ represents hydrogen, alkyl or acyl, and
$R^3$ represents quinuclidine or a group of the formula

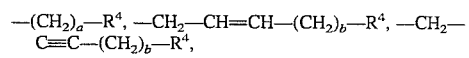

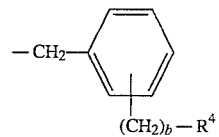

or

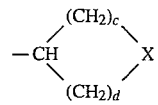

wherein
a denotes a number from 1 to 10,
b denotes a number 0, 1, 2, 3 or 4,
c denotes a number 0, 1 or 2,
d denotes a number 2 or 3, and
X denotes oxygen, sulphur or $NR^5$,
and their salts.

1 Claim, No Drawings

SUBSTITUTED BASIC 2-AMINOTETRALIN IN PHARMACEUTICALS

This is a division of application Ser. No. 07/891,485, filed May 29, 1992, now U.S. Pat. No. 5,298,513.

The invention relates to substituted basic 2-aminotetralins, processes for their preparation, and their use in medicaments.

It is known, from EP-A1-41 488, that 2-aminotetralins which are mono- or dialkyl-substituted on the nitrogen act on the central nervous system.

It is likewise known [Biochem. Pharmacol. 34 (6), 883–92] that 2-(N-2'-chloropropyl-N-propyl)amino-8-methoxy-1,2,3,4-tetrahydronaphthalene hydrochloride bonds irreversibly to various 5-HT receptor types.

In addition, 2-(N-3-hydroxypropyl-N-propyl)amino-8-methoxy-1,2,3,4-tetrahydronaphthalene is known as an intermediate for the preparation of substances which act on the central nervous system [Eur. J. Pharm. 127, 67–81, 1986].

New substituted basic 2-aminotetralins of the general formula (I)

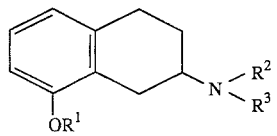

in which $R^1$ represents hydrogen or alkyl, $R^2$ represents hydrogen, alkyl or acyl, and $R^3$ represents quinuclidine or a group of the formula

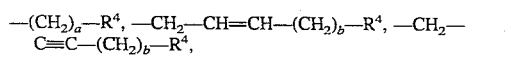

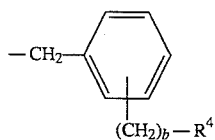

or

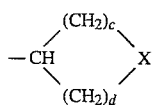

wherein a denotes a number from 1 to 10, b denotes a number 0, 1, 2, 3 or 4, c denotes a number 0, 1 or 2, d denotes a number 2 or 3, X denotes oxygen, sulphur or $NR^5$, where $R^5$ represents hydrogen or cycloalkyl, or represents alkyl which may be substituted by halogen, hydroxyl, amino, alkylamino, dialkylamino, carbamoyl or sulphamoyl or, represents aryl, heteroaryl, aralkyl, alkoxycarbonyl, alkylsulphonyl, phenylsulphonyl, tolylsulphonyl, benzylsulphonyl, formyl, carbamoyl or sulphamoyl, and $R^4$ denotes cyano or a group of the formula $-OR^6$, $-COOR^7$, $-CONR^8R^9$, $-SO_2NR^8R^9$, $-SO_mR^{10}$, $-NR^{11}R^{12}$,

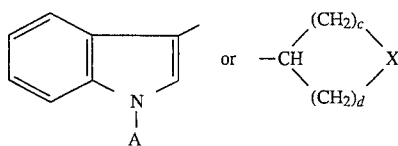

where c, d and X have the abovementioned meaning,

A represents hydrogen, alkylsulphonyl, phenylsulphonyl, tolylsulphonyl, benzylsulphonyl, acyl or alkoxycarbonyl, $R^6$ represents hydrogen, alkyl, alkenyl, cycloalkyl, aryl, aralkyl, acyl, alkoxycarbonyl, aryloxycarbonyl, aralkoxycarbonyl, tetrahydronapthalene-1-yl or benzothiadiazolyl, $R^7$ represents hydrogen, alkyl, alkenyl, aryl or aralkyl, $R^8$ and $R^9$ are identical or different and represent hydrogen, alkyl, aryl or aralkyl, $R^{10}$ represents alkyl, cycloalkyl, aryl or aralkyl, where the aryl radicals may be up to trisubstituted, identically or differently, by halogen, cyano, alkyl, alkoxy, trifluoromethyl or trifluoromethoxy, m represents a number 0, 1 or 2, $R^{11}$ and $R^{12}$ are identical or different and represent hydrogen, alkyl, aryl or aralkyl, where the aryl radicals may be substituted by halogen, cyano, alkyl, alkoxy or trifluoromethyl, or represent a group of the formula $-COR^{13}$ or $-SO_2R^{14}$, wherein $R^{13}$ denotes hydrogen, or an $NHR^{15}$ group, or denotes alkyl or alkoxy, or denotes aryl, aryloxy, aralkyl, aralkoxy or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, $R^{14}$ denotes cycloalkyl, or denotes alkyl which may be substituted by cyano, halogen, trifluoromethyl, trifluoromethoxy or alkoxycarbonyl, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino or denotes an $NR^8R^9$ group, where $R^8$ and $R^9$ have the abovementioned meaning and $R^{15}$ denotes hydrogen, or denotes cycloalkyl, or denotes alkyl which is optionally substituted by cyano, halogen, trifluoromethyl or trifluoromethoxy, or denotes aryl, aralkyl or heteroaryl where the aryl radicals may be up to trisubstituted, identically or differently, by alkyl, alkoxy, alkylthio, halogen, cyano, trifluoromethyl, trifluoromethoxy, trifluoromethylthio, amino, alkylamino or dialkylamino, or where $R^{11}$ and $R^{12}$, together with the nitrogen atom, form a ring from the series comprising

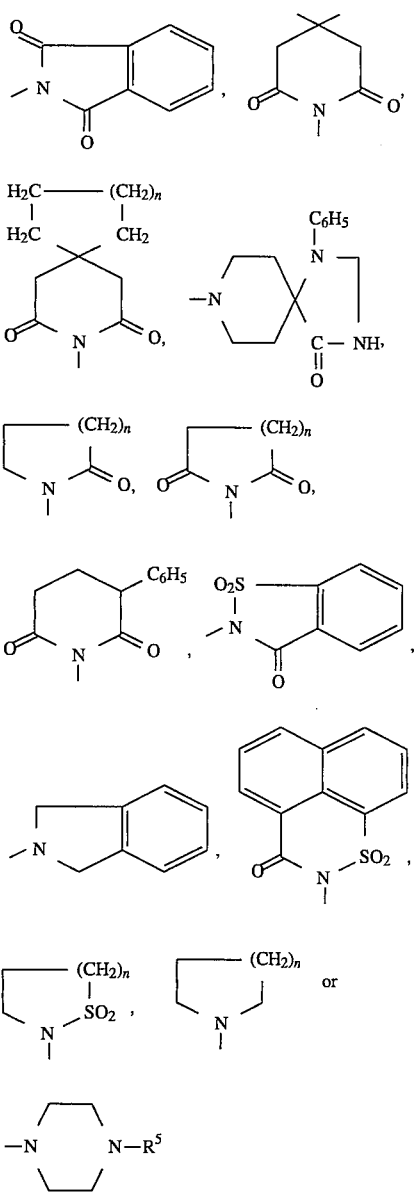

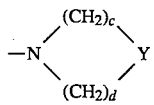

wherein
n denotes a number 1 or 2,
or in which
R² and R³, together with the nitrogen atom, form a group of the formula

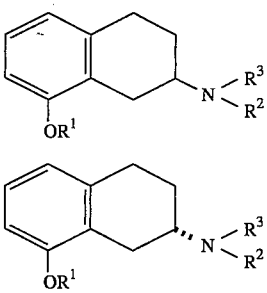

wherein
c and d have the abovementioned meaning, and
Y denotes oxygen, sulphur or a group of the formula $NR^5$ or $CH(CH_2)_e-NHR^5$, where
$R^5$ has the abovementioned meaning, and
e represents a number 0 to 4,
but where
$R^3$ does not denote 3-hydroxypropyl when $R^1$ represents methyl and $R^2$ represents propyl, and where
$R^3$ does not denote 2-methylthioethyl when
$R^1$ represents hydrogen or methyl and $R^2$ represents hydrogen, propyl or propionyl,
and their salts have been found.

Surprisingly, the substances according to the invention display a good action on the central nervous system and can be used for therapeutic treatment of humans and animals.

The substances according to the invention have several asymmetrical carbon atoms and can thus exist in various stereochemical forms. In addition, compounds having a sulphoxide group can likewise exist in different stereochemical forms. The invention relates both to the individual isomers and to their mixtures. The following isomeric forms of the substituted basic 2-aminotetralins may be mentioned as examples:

The substituted basic 2-aminotetralins according to the invention may also be present in the form of their salts. In general salts with inorganic or organic acids may be mentioned here.

In the context of the present invention, physiologically acceptable salts are preferred. Physiologically acceptable salts of the substituted basic 2-aminotetralines can be salts of the substances according to the invention with mineral acids, carboxylic acids or sulphonic acids. Particularly preferred salts, for example, are those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, oxalic acid, malonic acid, succinic acid, maleic acid, fumaric acid, malic acid, tartaric acid, citric acid or benzoic acid.

In general, alkyl represents a branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

In general, alkenyl represents a straight-chain or branched hydrocarbon radical having 2 to 12 carbon atoms and one or more, preferably one or two, double bonds. The lower alkyl radical having 2 to about 6 carbon atoms and one double bond is preferred. An alkenyl radical having 2 to 4 carbon atoms and one double bond is particularly preferred. Examples which may be mentioned are allyl, propenyl, isopropenyl, butenyl, isobutenyl, pentenyl, isopentenyl, hexenyl, isohexenyl, heptenyl, isoheptenyl, octenyl and isooctenyl.

In general, cycloalkyl represents a cyclic hydrocarbon radical having 5 to 8 carbon atoms. The cyclopentane and the cyclohexane ring are preferred. Examples may be mentioned are cyclopentyl, cyclohexyl, cycloheptyl and cyclooctyl.

In general, aryl represents an aromatic radical having 6 to about 12 carbon atoms. Preferred aryl radicals are phenyl, naphthyl and biphenyl.

In general, aralkyl represents an aryl radical, having 7 to 14 carbon atoms, which is bonded via an alkylene chain. Aralkyl radicals having 1 to 6 carbon atoms in the aliphatic part and 6 to 12 carbon atoms in the aromatic part are preferred. Examples which may be mentioned are the following aralkyl radicals: benzyl, naphthylmethyl, phenethyl and phenylpropyl.

In general, alkoxy represents a straight-chain or branched hydrocarbon radical, having 1 to 12 carbon atoms, which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

In general, aryloxy represents an aralkyl radical having 6 to about 12 carbon atoms, which is bonded via an oxygen atom. Preferred aryloxy radicals are phenoxy or naphthyloxy.

In general, aralkoxy represents an aralkyl radical having 7 to 14 carbon atoms, the alkylene chain being bonded via an oxygen atom. Aralkoxy radicals having 1 to 6 carbon atoms in the aliphatic part and 6 to 12 carbon atoms in the aromatic part are preferred. Examples which may be mentioned are the following aralkoxy radicals: benzyloxy, naphthylmethoxy, phenethoxy and phenylpropoxy.

In general, alkylthio represents a straight-chain or branched hydrocarbon radical, having 1 to 12 carbon atoms, which is bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio or isooctylthio.

In general, acyl represents phenyl or straight-chain or branched lower alkyl, having 1 to about 6 carbon atoms, which are bonded via a carbonyl group. Phenyl, and alkyl radicals having up to 4 carbon atoms are preferred. Examples which may be mentioned are: benzoyl, acetyl, ethylcarbonyl, propylcarbonyl, isopropylcarbonyl, butylcarbonyl and isobutylcarbonyl.

Alkoxycarbonyl may be represented, for example, by the formula

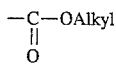

In this formula, alkyl represents a straight-chain or branched hydrocarbon radical having 1 to 12 carbon atoms. Lower alkoxycarbonyl having 1 to about 6 carbon atoms in the alkyl part is preferred. An alkoxycarbonyl having 1 to 4 carbon atoms in the alkyl part is particularly preferred. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

Aryloxycarbonyl may be represented, for example, by the formula —COO-aryl. In this formula, aryl represents, in general, an aromatic radical having 6 to 12 carbon atoms. Examples which may be mentioned are: phenoxycarbonyl and naphthyloxycarbonyl.

Aralkoxycarbonyl may be represented, for example, by the formula —COO-aralkyl. In this formula, aralkyl represents, in general, an aryl radical, having 7 to 14 carbon atoms, which is bonded via an alkylene chain, aralkyl radicals having 1 to 6 carbon atoms in the aliphatic part and 6 to 12 carbon atoms in the aromatic part being preferred. Examples which may be mentioned as aralkoxycarbonyl radicals are: benzyloxycarbonyl and naphthylmethyloxycarbonyl.

In the context of the abovementioned definition, heteroaryl represents, in general, a 5- to 6-membered aromatic ring, which may contain, as heteroatoms, oxygen, sulphur and/or nitrogen and to which a further aromatic ring may be fused. 5- and 6-membered aromatic rings which contain one oxygen, one sulphur and/or up to 2 nitrogen atoms and which are optionally fused to a benzyl group are preferred. The following may be mentioned as particularly preferred heteroaryl radicals: thienyl, furyl, pyridyl, pyrimidyl, pyrazinyl, pyridazinyl, quinolyl, isoquinolyl, quinazolyl, quinoxalyl, thiazolyl, benzothiazolyl, isothiazolyl, oxazolyl, benzoxazolyl, isoxazolyl, imidazolyl, benzimidazolyl, pyrazolyl and indolyl.

In general, halogen represents fluorine, chlorine, bromine or iodine, preferably fluorine, chlorine or bromine. Halogen particularly preferably represents fluorine or chlorine.

Preferred compounds of the general formula (I) are those in which $R^1$ represents hydrogen or lower alkyl, $R^2$ represents hydrogen, lower alkyl, lower alkylcarbonyl, or benzoyl, and $R^3$ represents quinuclidine or a group of the formula

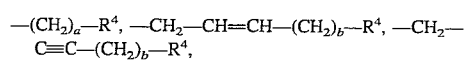

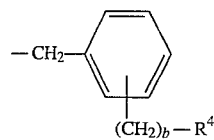

or

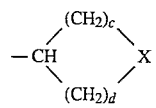

wherein a denotes a number 1 to 8, b denotes a number 0, 1, 2 or 3, c denotes a number 0, 1 or 2, d denotes a number 2 or 3, X denotes oxygen or the group $NR^5$, where $R^5$ represents hydrogen, or represents lower alkyl which is optionally substituted by hydroxyl or amino, or represents phenyl, benzyl, lower alkoxycarbonyl, lower alkylsulphonyl or carbamoyl, and $R^4$ denotes cyano or a group of the formula $-OR^6$, $-COOR^7$, $-CONR^8R^9$, $-SO_2NR^8R^9$, $-SO_mR^{10}$, $NR^{11}R_{12}$,

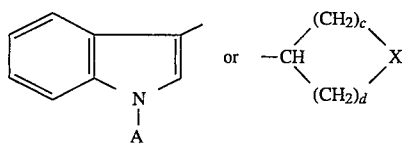 or 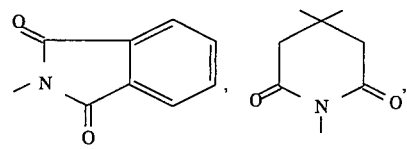

where
c, d and X have the abovementioned meaning,
A represents hydrogen, lower alkylsulphonyl, acetyl, phenylsulphonyl, tolylsulphonyl or lower alkoxycarbonyl, $R^6$ represents hydrogen, lower alkyl, phenyl, benzyl, lower alkylcarbonyl, lower alkoxycarbonyl or tetrahydronaphthalen-1-yl, $R^7$ represents hydrogen, lower alkyl or phenyl, $R^8$ and $R^9$ are identical or different and represent hydrogen, lower alkyl or phenyl, $R^{10}$ represents lower alkyl, or represents phenyl which may be up to disubstituted, identically or differently, by fluorine, chlorine, bromine, lower alkyl or lower alkoxy, m represents a number 0, 1 or 2, $R^{11}$ and $R^{12}$ are identical or different and represent hydrogen, lower alkyl, phenyl or benzyl, where the phenyl radicals may be substituted by fluorine, chlorine, bromine, lower alkyl, lower alkoxy or trifluoromethyl, or represent a group of the formula —$COR^{13}$ or —$SO_2R^{14}$, wherein $R^{13}$ denotes hydrogen, or denotes an $NHR^{15}$ group, or denotes lower alkyl or lower alkoxy, or denotes phenyl, benzyl, benzyloxy, thienyl, furyl, pyridyl, pyrimidyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, $R^{14}$ denotes cyclopropyl, cyclopentyl or cyclohexyl, or lower alkyl which is optionally substituted by cyano, fluorine, chlorine, bromine, trifluoromethyl or lower alkoxycarbonyl, or phenyl, benzyl, thienyl, furyl, pyrimidyl, pyridyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, or denotes an $NR^8R^9$ group, where $R^8$ and $R^9$ have the abovementioned meaning, and $R^{15}$ denotes lower alkyl which is optionally substituted by cyano, fluorine, chlorine or bromine, or denotes phenyl, benzyl, thienyl, furyl, pyridyl, pyrimidyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, or $R^{11}$ and $R^{12}$, together with the nitrogen atom, form a ring from the series comprising wherein
n denotes a number 1 or 2, or in which $R^2$ and $R^3$, together with the nitrogen atom, form a group of the formula wherein
c and d have the abovementioned meaning, and
Y denotes oxygen or an $NR^5$ or $CH(CH_2)_e$—$NHR^5$ group, where
$R^5$ has the abovementioned meaning, and
e represents a number 0, 1 or 2, but where
$R^3$ does not denote 3-hydroxypropyl when
$R^1$ represents methyl and $R^2$ represents propyl,
and R³ does not denote 2-methylthioethyl when
R¹ represents hydrogen or methyl and R² represents hydrogen, propyl or propionyl,
and their salts.

Particularly preferred compounds of the general formula (I) are those in which

R¹ represents hydrogen or methyl,
R² represents hydrogen, methyl, ethyl, propyl, isopropyl, acetyl or propionyl, and
R³ represents quinuclidine or a group of the formula

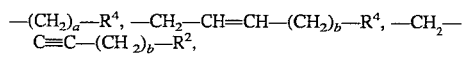

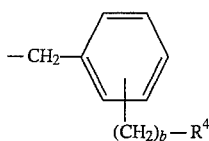

or

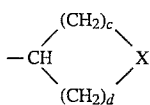

wherein
a denotes a number 1 to 6,
b denotes a number 0, 1 or 2,
c denotes a number 1 or 2,
d denotes the number 2,
X denotes the NR⁵ group, where
　R⁵ represents hydrogen, methyl, ethyl, propyl, isopropyl, butyl, isobutyl, phenyl, benzyl, methoxycarbonyl, ethoxycarbonyl, propoxycarbonyl, isopropoxycarbonyl, methylsulphonyl, ethylsulphonyl or carbamoyl,
and
R⁴ denotes cyano or a group of the formula —OR⁶, —COOR⁷, —CONR⁸R⁹, —SO_mR¹⁰, —NR¹¹R¹²,

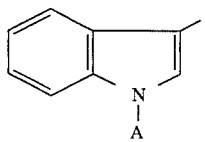 or 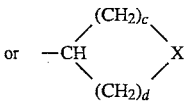

where
c, d and X have the abovementioned meaning,
A represents hydrogen, methylsulphonyl, phenylsulphonyl, tolylsulphonyl, methoxycarbonyl or ethoxycarbonyl,
R⁶ represents hydrogen, methyl, ethyl, propyl, isopropyl, butyl, isobutyl, acetyl, ethylcarbonyl, propylcarbonyl, methoxycarbonyl, ethoxycarbonyl, propoxycarbonyl, isopropoxycarbonyl, butoxycarbonyl, isobutoxycarbonyl or tetrahydronaphthalen-1-yl,
R⁷ represents hydrogen, methyl, ethyl, propyl, isopropyl, butyl or isobutyl,
R⁸ and R⁹ are identical or different and represent hydrogen, methyl, ethyl, propyl, isopropyl, butyl or isobutyl,
R¹⁰ represents methyl, ethyl, propyl, isopropyl, butyl, isobutyl, or represents phenyl which is optionally substituted by fluorine, chlorine, methyl, ethyl, propyl or isopropyl,
m represents a number 0, 1 or 2,
R¹¹ and R¹² are identical or different, and represent hydrogen, methyl, ethyl, propyl, isopropyl, butyl, isobutyl, or represent phenyl which is optionally substituted by fluorine, chlorine, methyl or methoxy, or represent a —COR¹³ or —SO₂R¹⁴ group, wherein
R¹³ denotes an NHR¹⁵ group, or denotes methyl, ethyl, propyl, isopropyl, methoxy, ethoxy, propoxy or isopropoxy, or denotes phenyl, benzyl, benzyloxy, thienyl, furyl, pyridyl, pyrimidyl, quinolyl or isoquinolyl which are optionally substituted by methyl, methoxy, fluorine or chlorine,
R¹⁴ denotes methyl, ethyl, propyl, isopropyl, butyl or isobutyl which are optionally substituted by fluorine, chlorine, methoxycarbonyl, ethoxycarbonyl, propoxycarbonyl, isopropoxycarbonyl, butoxycarbonyl or isobutoxycarbonyl, or denotes phenyl, thienyl, furyl, pyridyl, pyrimidyl, quinolyl or isoquinolyl which are optionally substituted by methyl, ethyl, propyl, isopropyl, methoxy, fluorine or chlorine, or denotes an NR⁸R⁹ group, where R⁸ and R⁹ have the abovementioned meaning, and
R¹⁵ denotes methyl, ethyl, propyl, isopropyl, butyl, isobutyl, pentyl, isopentyl, hexyl or isohexyl which are optionally substituted by fluorine or chlorine, or denotes phenyl which may be substituted by fluorine, chlorine, methyl or methoxy, or R¹¹ and R¹², together with the nitrogen atom, form a ring from the series comprising

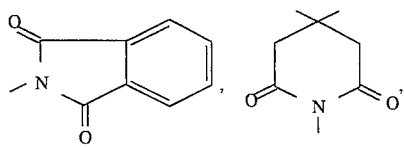

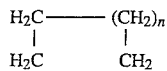

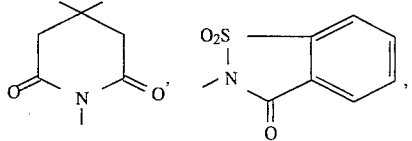

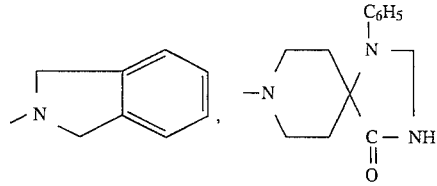

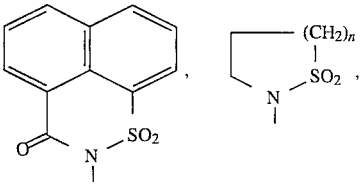

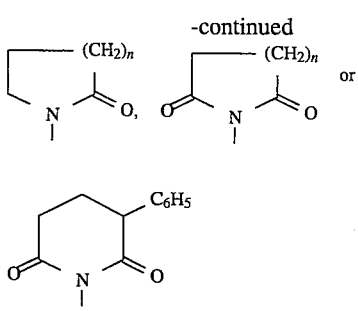

wherein
n denotes a number 1 or 2,
or in which
R² and R³, together with the nitrogen atom, form a group of the formula

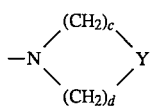

wherein
c and d have the abovementioned meaning, and
Y denotes a group of the formula NR⁵ or CH(CH₂)$_e$—NHR⁵ where
R⁵ has the abovementioned meaning and
e represents a number 1 or 2,
but where
R³ does not denote 3-hydroxypropyl when
R¹ represents methyl and R² represents propyl,
and
R³ does not denote 2-methylthioethyl when
R¹ represents hydrogen or methyl and R² represents hydrogen, propyl or propionyl,
and their salts.

Particularly preferred compounds of the general formula (I) are those which contain a basic nitrogen. Basic nitrogen is taken to mean nitrogen groups, for ample amino groups, which are not deactivated. A nitrogen group can be deactivated by electron-attracting groups. Such deactivating groups may be acyl or sulphonyl groups which are bonded to the nitrogen. These preferably include alkyl-, aryl- or aralkylcarbonyl groups, alkyl-, aryl- or aralkylsulphonyl or -sulphamoyl groups, carboxyl, carbamoyl or alkoxy-, aryloxy- or aralkoxycarbonyl groups.

Examples which may be mentioned are the following substituted basic 2-aminotetralins:

N-6-Chlorohexyl-N'-{3-[N-(8-methoxy-1,2,3,4-tetrahydro-2-naphthyl)-N-propyl]amino}propylurea
8-Methoxy-2-[N-propyl-N-(3-phthalimidoyl-propyl)]amino-1,2,3,4-tetrahydronaphthalene
2-(2-Ethoxycarbonylamido-ethyl)amino-8-methoxy-1,2,3,4-tetrahydronaphthalene
2-[N-(Diethylcarboxamidoethyl)-N-propyl]amino-8-methoxy-1,2,3,4-tetrahydronaphthalene
2-{N-[3-(4-Fluorobenzenesulphonamido)propyl]-N-propyl}amino-8-methoxy-1,2,3,4-tetrahydronaphthalene
2-[N-(3-Aminopropyl)-N-propyl]amino-8-methoxy-1,2,3,4-tetrahydronaphthalene
8-Methoxy-2-[N-(2-toluenesulphonamidoethyl)-N-propyl]amino-1,2,3,4-tetrahydronaphthalene
2-{4-[N-(8-Methoxy-1,2,3,4-tetrahydronaphthalen-2-yl)-N-propyl]amino-butyl}-1,2-benzoisothiazol-3(2H)-one 1,1-dioxide
2-[N-(2-Methanesulphonamido-ethyl)-N-propyl]amino-8-methoxy-1,2,3,4-tetrahydronaphthalene
2-[N-(2-Aminoethyl)-N-propyl]amino-8-methoxy-1,2,3,4-tetrahydronaphthalene
2-(N-Ethoxycarbonylmethyl-N-propyl)amino-8-methoxy-1,2,3,4-tetrahydronaphthalene
2-(N-Cyanomethyl-N-propyl)amino-8-methoxy-1,2,3,4-tetrahydronaphthalene
N-{2-[N-(8-Methoxy-1,2,3,4-tetrahydronaphthalen-2-yl)-N-propyl]amino}ethyl-N'-phenylurea
8-Methoxy-2-[N-propyl-N-(2-nicotinoylamino-ethyl)]amino-1,2,3,4-tetrahydronaphthalene
2-{N-[2-(3-Chloropropylsulphonamido)ethyl]-N-propyl}amino-8-methoxy-1,2,3,4-tetrahydronaphthalene
2{N-[2-(4-Chlorobutylsulphonamido)ethyl]-N-propyl}amino-8-methoxy-1,2,3,4-tetrahydronaphthalene
2-[N-(2-Dimethylaminosulphonylamido)ethyl-N-propyl]amino-8-methoxy-1,2,3,4-tetrahydronaphthalene
2-[N-(2-Cyanoethyl)-N-propyl]amino-8-methoxy-1,2,3,4-tetrahydronaphthalene
2-[N-(2-Carboxamido-ethyl)-N-propyl]amino-8-methoxy-1,2,3,4-tetrahydronaphthalene
2-[N-(2-Ethyl-carbonyldioxy-ethyl)-N-propyl]amino-8-methoxy-1,2,3,4-tetrahydronaphthalene
2-{2-[N-Propyl-N-(8-methoxy-1,2,3,4-tetrahydronaphthalen-2-yl)]amino}ethyl-perhydrothiazine 1,1-dioxide
2-{2-[N-propyl-N-(8-methoxy-1,2,3,4-tetrahydronaphthalen-2-yl)]amino}ethyl-isothiazolidine 1,1-dioxide
2-(4-Methylpiperazin-1-yl)-8-methoxy-1,2,3,4-tetrahydronaphthalene
2-(N-Quinuclidin-3-yl-N-propyl)amino-8-methoxy-1,2,3,4-tetrahydronaphthalene
2-(N-Diethylcarboxamidomethyl-N-propyl)amino-8-methoxy-1,2,3,4-tetrahydronaphthalene
2-[N-(2-Methoxycarbonylamido-ethyl)-N-propyl]amino-8-methoxy-1,2,3,4-tetrahydronaphthalene
2-(2-Diethylaminoethyl)amino-8-methoxy-1,2,3,4-tetrahydronaphthalene
2-[N-(2-Methylaminoethyl)-N-propyl]amino-8-methoxy-1,2,3,4-tetrahydronaphthalene
2-[N-(2-Diethylaminoethyl)-N-propyl]amino-8-methoxy-1,2,3,4-tetrahydronaphthalene
2-(1-Ethoxycarbonyl-piperidin-4-yl)amino-8-methoxy-1,2,3,4-tetrahydronaphthalene
2-(4-Ethoxycarbonylaminomethyl)piperidin-1-yl-8-methoxy-1,2,3,4-tetrahydronaphthalene
2-(3-Dimethylaminopropyl)amino-8-methoxy-1,2,3,4-tetrahydronaphthalene
2-[N-(3-Dimethylaminopropyl)-N-propyl]amino-8-methoxy-1,2,3,4-tetrahydronaphthalene
2-(1-Methylpiperidin-4-yl)amino-8-methoxy-1,2,3,4-tetrahydronaphthalene
2-[N-(3-Dimethylaminopropyl)-N-propionyl]amino-8-methoxy-1,2,3,4-tetrahydronaphthalene
2-[N-(2-Diethylaminoethyl)-N-acetyl]amino-8-methoxy-1,2,3,4-tetrahydronaphthalene
N-6-Chlorohexyl-N'-{3-[N-(8-methoxy-1,2,3,4-tetrahydro-2-naphthyl)-N-propyl]amino}propylurea hydrochloride
8-Methoxy-2-[N-propyl-N-(3-phthalimidoyl-propyl)]amino-1,2,3,4-tetrahydronaphthalene hydrochloride
2-(2-Ethoxycarbonylamido-ethyl)amino-8-methoxy-1,2,3,4-tetrahydronaphthalene hydrochloride
2-[N-(Diethylcarboxamidoethyl)-N-propyl]amino-8-methoxy-1,2,3,4-tetrahydronaphthalene hydrochloride 2-{N-[3-(4-Fluorobenzenesulphonamido)propyl]-N-propyl}amino-8-methoxy-1,2,3,4-tetrahydronaphthalene hydrochloride
8-Methoxy-2-[N-(2-toluenesulphonamidoethyl)-N-propyl]amino-1,2,3,4-tetrahydronaphthalene hydrochloride
2-[N-(2-Methanesulphonamido-ethyl)-N-propyl]amino-8-methoxy-1,2,3,4-tetrahydronaphthalene hydrochloride
2-[N-(2-Aminoethyl)-N-propyl]amino-8-methoxy-1,2,3,4-tetrahydronaphthalene dihydrochloride
2-(N-Cyanomethyl-N-propyl)amino-8-methoxy-1,2,3,4-tetrahydronaphthalene hydrochloride
N-{2-[N-(8-methoxy-1,2,3,4-tetrahydronaphthalen-2-yl)-N-propyl]amino}ethyl-N'-phenylurea hydrochloride
8-Methoxy-2-[N-propyl-N-(2-nicotinoylamino-ethyl)]amino-1,2,3,4-tetrahydronaphthalene hydrochloride
2-{N-[2-(3-Chloropropylsulphonamido)ethyl]-N-propyl}amino-8-methoxy- 1,2,3,4-tetrahydronaphthalene dihydrochloride
2-{N-[2-(4-Chlorobutylsulphonamido)ethyl]-N-propyl}amino-8-methoxy-1,2,3,4-tetrahydronaphthalene hydrochloride
2-[N-(2-Dimethylaminosulphonlamido)ethyl-N-propyl]amino-8-methoxy-1,2,3,4-tetrahydronaphthalene hydrochloride
2-[N-(2-Cyanoethyl)-N-propyl]amino-8-methoxy-1,2,3,4-tetrahydronaphthalene hydrochloride
2-[N-(2-Carboxamido-ethyl)-N-propyl]amino-8-methoxy-1,2,3,4-tetrahydronaphthalene hydrochloride
2-[N-(2-Ethyl-carbonyldioxy-ethyl)-N-propyl]amino-8-methoxy-1,2,3,4-tetrahydronaphthalene hydrochloride
2-{2-[N-Propyl-N-(8-methoxy-1,2,3,4-tetrahydronaphthalen-2-yl)]amino}ethyl-perhydrothiazine 1,1-dioxide hydrochloride
2-{2-[N-Propyl-N-(8-methoxy-1,2,3,4-tetrahydronaphthalen-2-yl)]amino}ethyl-isothiazolidine 1,1-dioxide hydrochloride
2-(4-Methylpiperazin-1-yl)-8-methoxy-1,2,3,4-tetrahydronaphthalene hydrochloride
2-(N-Quinuclidin-3-yl-N-propyl)amino-8-methoxy-1,2,3,4-tetrahydronaphthalene dihydrochloride
2-(N-Diethylaminocarboxamidomethyl-N-propyl)amino-8-methoxy-1,2,3,4-tetrahydronaphthalene dihydrochloride
2-[N-(2-Methoxycarbonylamido-ethyl)-N-propyl]amino-8-methoxy-1,2,3,4-tetrahydronaphthalene hydrochloride
2-(2-Diethylaminoethyl)amino-8-methoxy-1,2,3,4-tetrahydronaphthalene hydrochloride
2-[N-(2-Methylaminomethyl)-N-propyl]amino-8-methoxy-1,2,3,4-tetrahydronaphthalene dihydrochloride
2-[N-(2-Diethylaminoethyl)-N-propyl]amino-8-methoxy-1,2,3,4-tetrahydronaphthalene dihydrochloride
2-(1-Carbethoxypiperidin-4-yl)amino-8-methoxy-1,2,3,4-tetrahydronaphthalene hydrochloride
2-(4-Ethoxycarbonylamido-methyl)piperidin-1-yl-8-methoxy-1,2,3,4-tetrahydronaphthalene hydrochloride
2-(3-Dimethylaminopropyl)amino-8-methoxy-1,2,3,4-tetrahydronaphthalene hydrochloride
2-[N-(3-Dimethylaminopropyl)-N-propyl]amino-8-methoxy-1,2,3,4-tetrahydronaphthalene dihydrochloride
2-(1-Methylpiperidin-4-yl)amino-8-methoxy-1,2,3,4-tetrahydronaphthalene dihydrochloride
2-[N-(3-Dimethylaminopropyl)-N-propionyl]amino-8-methoxy-1,2,3,4-tetrahydronaphthalene dihydrochloride
2-[N-(2-Diethylaminoethyl)-N-acetyl]amino-8-methoxy-1,2,3,4-tetrahydronaphthalene hydrochloride Furthermore, a process for the preparation of the substituted basic 2-aminotetralins, according to the invention, of the formula (I)

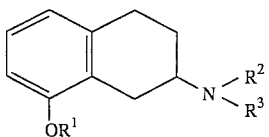

in which
R$^1$ represents hydrogen or alkyl,
R$^2$ represents hydrogen, alkyl or acyl, and
R$^3$ represents quinuclidine or a group of the formula

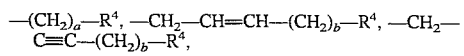

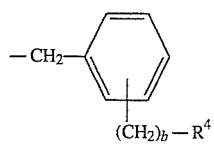

or

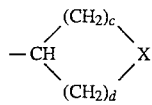

wherein
a denotes a number from 1 to 10,
b denotes a number 0, 1, 2, 3 or 4,
c denotes a number 0, 1 or 2,
d denotes a number 2 or 3,
X denotes oxygen, sulphur or NR$^5$, where
R$^5$ represents hydrogen or cycloalkyl, or represents alkyl which may be substituted by halogen, hydroxyl, amino, alkylamino, dialkylamino, carbamoyl or sulphamoyl, or represents aryl, heteroaryl, aralkyl, alkoxy carbonyl, alkylsulphonyl, phenylsulphonyl, tolylsulphonyl, benzylsulphonyl, formyl, carbamoyl or sulphamoyl,
and
R$^4$ denotes cyano or a group of the formula —OR$^6$, —COOR$^7$, —CONR$^8$R$^9$, —SO$_2$NR$^8$R$^9$, —SO$_m$R$^{10}$, —NR$^{11}$R$^{12}$,

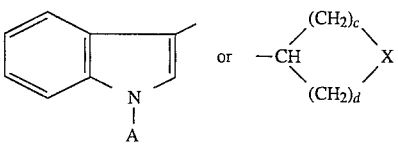

where
c, d and X have the abovementioned meaning, A represents hydrogen, alkylsulphonyl, phenylsulphonyl, tolylsulphonyl, benzylsulphonyl, acyl or alkoxycarbonyl,
R$^6$ represents hydrogen, alkyl, alkenyl, cycloalkyl, aryl, aralkyl, acyl, alkoxycarbonyl, aryloxycarbonyl, aralkoxycarbonyl, tetrahydronaphthalen-1-yl or benzothiadiazolyl,
R$^7$ represents hydrogen, alkyl, alkenyl, aryl or aralkyl,
R$^8$ and R$^9$ are identical or different and represent hydrogen, alkyl, aryl or aralkyl,
R$^{10}$ represents alkyl, cycloalkyl, aryl or aralkyl, where the aryl radicals may be up to trisubstituted, identically or differently, by halogen, cyano, alkyl, alkoxy, trifluoromethyl or trifluoromethoxy, m represents a number 0, 1 or 2, $R^{11}$ and $R^{12}$ are identical or different and represent hydrogen, alkyl, aryl or aralkyl, where the aryl radicals may be substituted by halogen, cyano, alkyl, alkoxy or trifluoromethyl, or represent a group of the formula —$COR^{13}$ or —$SO_2R^{14}$, wherein $R^{13}$ denotes hydrogen, or denotes an $NHR^{15}$ group, or denotes alkyl or alkoxy, or denotes aryl, aryloxy, aralkyl, aralkoxy or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, $R^{14}$ denotes cycloalkyl, or denotes alkyl which may be substituted by cyano, halogen, trifluoromethyl, trifluoromethoxy or alkoxycarbonyl, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino or denotes an $NR^8R^9$ group, where $R^8$ and $R^9$ have the abovementioned meaning and $R^{15}$ denotes hydrogen, or denotes cycloalkyl, or denotes alkyl which is optionally substituted by cyano, halogen, trifluoromethyl or trifluoromethoxy, or denotes aryl, aralkyl or heteroaryl where the aryl radicals may be up to trisubstituted, identically or differently, by alkyl, alkoxy, alkylthio, halogen, cyano, trifluoromethyl, trifluoromethoxy, trifluoromethylthio, amino, alkylamino or dialkylamino, or where $R^{11}$ and $R^{12}$, together with the nitrogen atom, form a ring from the series comprising

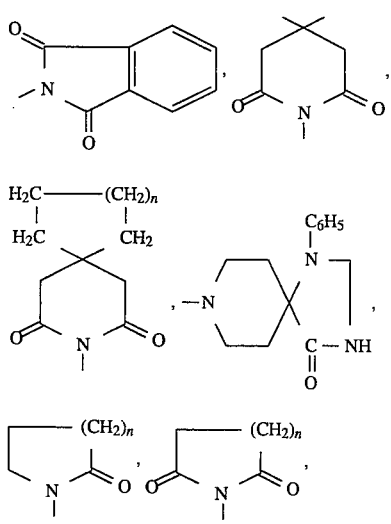

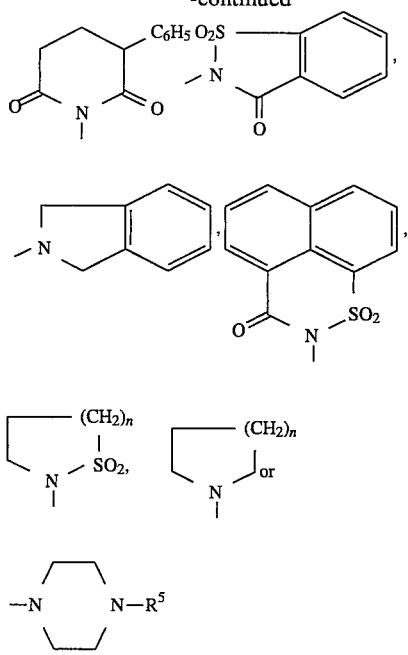

wherein n denotes a number 1 or 2, or in which $R^2$ and $R^3$, together with the nitrogen atom, form a group of the formula

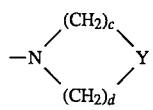

wherein c and d have the abovementioned meaning, and

Y denotes oxygen, sulphur or a group of the formula $NR^5$ or $CH(CH_2)_e$—$NHR^5$, where $R^5$ has the abovementioned meaning, and e represents a number 0 to 4, but where $R^3$ does not denote 3-hydroxypropyl when $R^1$ represents methyl and $R^2$ represents propyl, and where $R^3$ does not denote 2-methylthioethyl when $R^1$ represents hydrogen or methyl and $R^2$ represents hydrogen, propyl or propionyl, and their salts, has been found, which is characterized in that tetralones of the general formula (II)

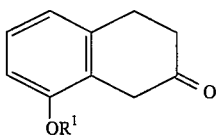

(II)

in which $R^1$ has the meaning mentioned, are reacted with amines of the general formula (III)

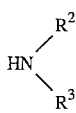

(III)

in which

R² and R³ have the meaning mentioned, but R² may not represent acyl, in inert solvents, if appropriate in the presence of auxiliaries, the intermediates are then reduced in inert solvents, then, in the case of the preparation of the acyl compounds (R²=acyl), reacted with an acylating agent, then, if appropriate, functional groups are converted into other functional groups by reduction, hydrolysis, oxidation or reaction with electrophilic reagents and then, in the case of the preparation of the salts, reacted with the appropriate acid.

The process according to the invention may be described, for the case of the reaction with cyclic amines, by equation (a) and, for the case of the reaction with open-chain amines, by equation (b):

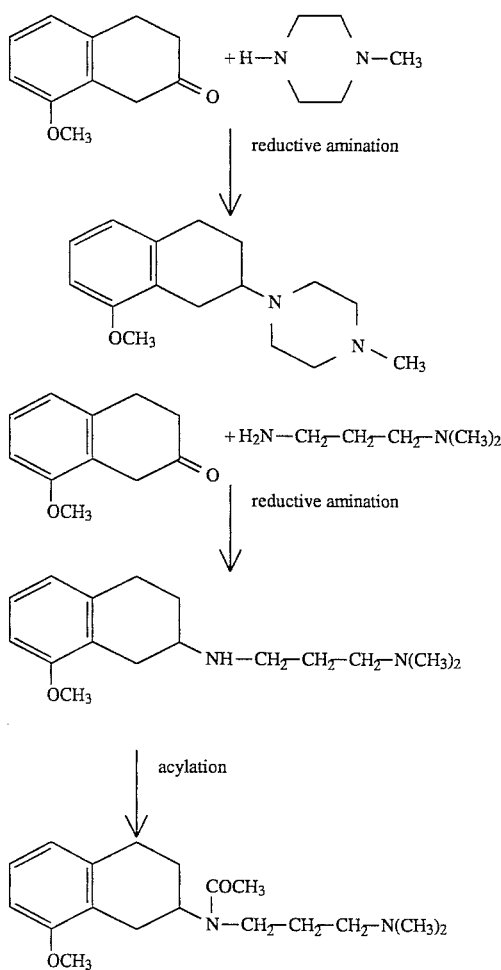

The tetralones, of the general formula (II), used as starting materials are known or can be prepared by known methods [P. A. Robins, J. Walker, J. Chem. Soc. 1958, 409; Cornforth et al. J. Chem. Sec. 1942, 689].

The amines, of the general formula (III), used as starting compounds are known or can be prepared by known methods [Houben-Weyl's "Methoden der organischen Chemie" (Methods of Organic Chemistry) vol. XI/1 and XI/2].

In the case of the reaction with primary amines the intermediates are Schiff bases, and in the case of the reaction with secondary amines the intermediates are enamines or immonium salts.

The intermediates are prepared by reaction of the tetralones (II) with amines (III) in inert organic solvents, if appropriate in the presence of a catalyst and if appropriate in the presence of a dehydrating agent.

The process according to the invention can be carried out in two steps, i.e. with isolation of the intermediates. It is also possible to carry out the process according to the invention as a one-pot process.

Suitable inert solvents here are those conventional organic solvents which do not change under the reaction conditions. These preferably include alcohols such as methanol, ethanol, propanol or isopropanol, or ethers such as diethyl ether, butyl methyl ether, dioxane, tetrahydrofuran, glycol dimethyl ether or diethylene glycol dimethyl ether, or halogenated hydrocarbons such as, for example, methylene chloride, chloroform or carbon tetrachloride, or hydrocarbons such as benzene, toluene, xylene, or petroleum fractions, or amides such as dimethylformamide or hexamethylphosphoric triamide, or acetic acid.

In addition, it is possible to use mixtures of the solvents mentioned.

In general, protonic acids are used as catalysts. These preferably include inorganic acids such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$ alkyl radicals or having aryl radicals, such as, for example, methanesulphonic acid, ethanesulphonic acid, benzenesulphonic acid or toluenesulphonic acid.

The water formed during the reaction may be removed, if appropriate, as a mixture with the solvent used during or after the reaction, for example by distillation or by addition of dehydrating agents, such as, for example, phosphorus pentoxide or, preferably, by molecular sieve.

The reaction is generally carried out in a temperature range from 0° C. to +150° C., preferably from +20° C. to +100° C.

In the case of removal of the water formed during the reaction by azeotropic distillation with the solvents used, the reaction is preferably carried out at the boiling temperature of the azeotrope.

The reaction can be carried out at atmospheric, increased or reduced pressure (e.g. 0.5–5 bar). In general, the reaction is carried out at atmospheric pressure.

When carrying out the reaction, the starting compounds are generally employed in a tetralone (II) to amine (III) molar ratio of 0.5:2 to 1:2. Molar amounts of the reactants are used preferably.

The intermediates are reduced either by hydrogen in water or inert organic solvents such as alcohols, ethers or halogenated hydrocarbons, or mixtures thereof, using catalysts such as Raney nickel, palladium, palladium on animal charcoal, or platinum, or using hydrides in inert solvents, if appropriate in the presence of a catalyst.

The reaction is preferably carried out using hydrides, such as complex borohydrides or aluminium hydrides. Sodium borohydride, lithium aluminum hydride or sodium cyanoborohydride are particularly preferably employed here.

Suitable solvents here are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, or amides such as hexamethylphosphoric triamide, or dimethylformamide, or acetic acid. It is also possible to use mixtures of the solvents mentioned.

In general, protonic acids are used as catalysts during the reduction. These preferably include inorganic acids such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or having aryl radicals, such as, for example, methanesulphonic acid, ethanesulphonic acid, benzenesulphonic acid or toluenesulphonic acid.

When carrying out the process according to the invention, it has proven favorable to carry out the reaction of the tetralones (II) with the amines (III) in an inert solvent, preferably in ethyl acetate or in alcohols such as, for example, methanol, ethanol, propanol or isopropanol, or mixtures thereof, in the presence of inorganic or organic acids, such as, for example, hydrochloric acid or acetic acid, and in the presence of a reducing agent, preferably complex hydrides such as, for example, sodium borohydride or sodium cyanoborohydride, if appropriate in the presence of a dehydrating agent, preferably molecular sieve, as a one-pot process.

In this case, the reaction is carried out in a temperature range from 0° C. to +150° C., preferably from 0° C. to +100° C., at atmospheric pressure. It is also possible to carry out the reaction at a reduced pressure or at an increased pressure (e.g. in a Carius tube).

If the process according to the invention is carried out as a one-pot reaction, it has proved favorable to employ the amine in an excess of up to 10-fold, preferably up to 5-fold, to the tetralone.

In general, the acylation is carried out in inert solvents by reaction of the compounds according to the invention, having $R^2$=H, with acylating agents, preferably reactive carboxylic acid derivatives, if appropriate in the presence of bases.

Inert solvents here are, in general, water or organic solvents which do not change under the reaction conditions. These preferably include alcohols such as methanol, ethanol, propanol or isopropanol, or ethers such as diethyl ether, tetrahydrofuran, dioxane or glycol dimethyl ether, or hydrocarbons such as benzene, toluene, xylene or petroleum fractions, or halogenated hydrocarbons such as methylene chloride, chloroform or carbon tetrachloride, or carboxylic acids such as acetic acid or propionic acid, or carboxylic acid anhydrides such as propionic anhydride or acetic anhydride. It is also possible to employ mixtures of the solvents mentioned.

Reactive carboxylic acid derivatives are, in general, carboxylic acid halides or carboxylic acid anhydrides. Aliphatic carboxylic acid bromides, chlorides or anhydrides are preferred here. Acetyl chloride, acetyl bromide, acetic anhydride, propionyl chloride, propionyl bromide and propionic anhydride are particularly preferred.

Conventional basic compounds can be employed as bases for basic reactions. These preferably include allaki metal or alkaline earth metal hydroxides or carbonates, such as, for example, lithium hydroxide, sodium hydroxide, potassium hydroxide or barium hydroxide, sodium carbonate or potassium carbonate, or alkali metal alcoholates such as, for example, sodium methanolate, sodium ethanolate, potassium methanolate or potassium ethanolate.

In general, the acylation is carried out in a temperature range from −20° C. to +100° C., preferably from 0° C. to +50° C., at atmospheric pressure.

In the context of the present invention, the disubstituted 2-aminotetralins (Ia) correspond to the general formula

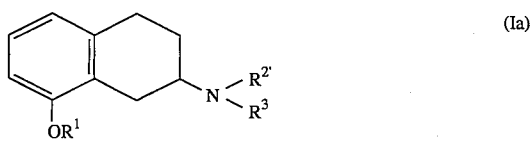

in which $R^1$ and $R^3$ have the meaning mentioned and $R^{2'}$ represents alkyl.

In the context of the present invention, the alkyl-substituted 2-aminotetralins (Ib) correspond to the general formula

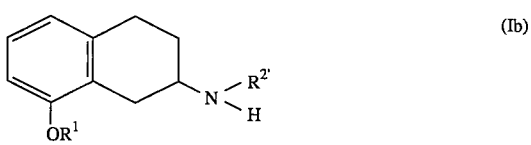

in which $R^1$ has the abovementioned meaning and $R^{2'}$ represents alkyl.

In the context of the present invention, the monosubstituted basic 2-aminotetralins (Ic) correspond to the formula

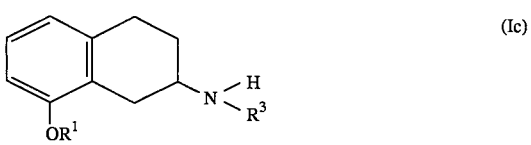

in which $R^1$ and $R^3$ have the meaning mentioned.

A further process for the preparation of the compounds of the general formula (Ia) has been found, starting from the compounds of the formulae (Ib) and (Ic) according to the invention, in which process the starting compounds (Ib) and (Ic) are obtained by the abovementioned process, according to the invention, of reductive amination.

The compounds of the general formula (Ia)

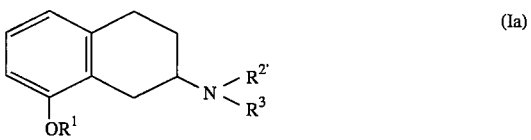

in which $R^1$ represents hydrogen or alkyl, $R^{2'}$ represents alkyl, $R^3$ represents quinuclidine or a group of the formula

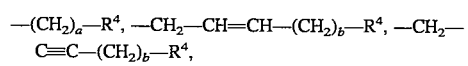

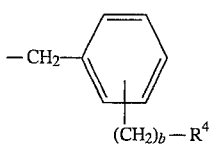

or

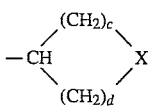

wherein a denotes a number from 1 to 10,
b denotes a number 0, 1, 2, 3 or 4,
c denotes a number 0, 1 or 2,
d denotes a number 2 or 3,
X denotes oxygen, sulphur or $NR^5$, where
  R represents hydrogen or cycloalkyl, or represents alkyl which may be substituted by halogen, hydroxyl, amino, alkylamino, dialkylamino, carbamoyl or sulphamoyl or, represents aryl, heteroaryl, aralkyl, alkoxycarbonyl, alkylsulphonyl, phenylsulphonyl, tolylsulphonyl, benzylsulphonyl, formyl, carbamoyl or sulphamoyl, and $R^4$ denotes cyano or a group of the formula $-OR^6$, $-COOR^7$, $-CONR^8R^9$, $-SO_2NR^8R^9$, $-SO_mR^{10}$, $-NR^{11}R^{12}$,

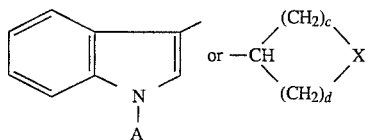

where c, d and X have the abovementioned meaning,
A represents hydrogen, alkylsulphonyl, phenylsulphonyl, tolylsulphonyl, benzylsulphonyl, acyl or alkoxycarbonyl,
$R^6$ represents hydrogen, alkyl, alkenyl, cycloalkyl, aryl, aralkyl, acyl, alkoxycarbonyl, aryloxycarbonyl, aralkoxycarbonyl, tetrahydronaphthalen-1-yl or benzothiadiazolyl,
$R^7$ represents hydrogen, alkyl, alkenyl, aryl or aralkyl,
$R^8$ and $R^9$ are identical or different and represent hydrogen, alkyl, aryl or aralkyl,
$R^{10}$ represents alkyl, cycloalkyl, aryl or aralkyl, where the aryl radicals may be up to trisubstituted, identically or differently, by halogen, cyano, alkyl, alkoxy, trifluoromethyl or trifluoromethoxy,
m represents a number 0, 1 or 2,
$R^{11}$ and $Rn12$ are identical or different and represent hydrogen, alkyl, aryl or aralkyl, where the aryl radicals may be substituted by halogen, cyano, alkyl, alkoxy or trifluoromethyl, or represent a group of the formula $-COR^{13}$ or $-SO_2R^{14}$, wherein
  $R^{13}$ denotes hydrogen, or denotes an $NHR^{15}$ group, or denotes alkyl or alkoxy, or denotes aryl, aryloxy, aralkyl, aralkoxy or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino,
  $R^{14}$ denotes cycloalkyl, or denotes alkyl which may be substituted by cyano, halogen, trifluoromethyl, trifluoromethoxy or alkoxycarbonyl, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino or denotes an $NR^8R^9$ group, where
    $R^8$ and $R^9$ have the abovementioned meaning
  and
  $R^{15}$ denotes hydrogen, or denotes cycloalkyl, or denotes alkyl which is optionally substituted by cyano, halogen, trifluoromethyl or trifluoromethoxy, or denotes aryl, aralkyl or heteroaryl where the aryl radicals may be up to trisubstituted, identically or differently, by alkyl, alkoxy, alkylthio, halogen, cyano, trifluoromethyl, trifluoromethoxy, trifluoromethylthio, amino, alkylamino or dialkylamino, or where $R^{11}$ and $R^{12}$, together with the nitrogen atom, form a ring from the series comprising

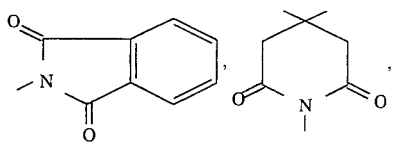

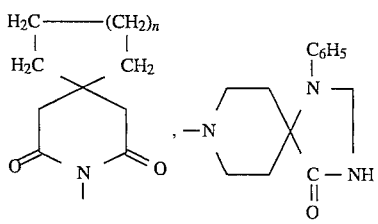

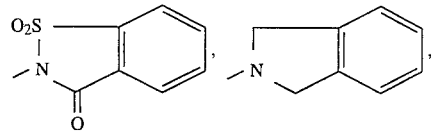

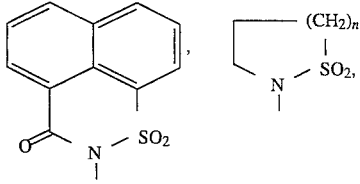

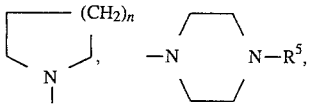

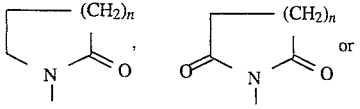

-continued

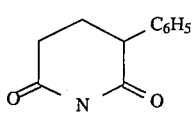

wherein n denotes a number 1 or 2, or in which

R² and R³, together with the nitrogen atom, form a group of the formula

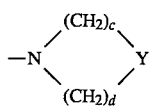

wherein c and d have the abovementioned meaning, and

Y denotes oxygen, sulphur or a group of the formula NR⁵ or CH(CH₂)$_e$—NHR⁵, where R⁵ has the abovementioned meaning, and e represents a number 0 to 4, but where R³ does not denote 3-hydroxypropyl when R¹ represents methyl and R² represents propyl, and where R³ does not denote 2-methylthioethyl when R¹ represents hydrogen or methyl and R² represents propyl, and their salts can be prepared by

[A] reacting alkyl-substituted 2-aminotetralins of the general formula (Ib)

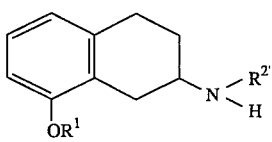 (Ib)

in which

R¹ and R²' have the abovementioned meaning, with halogen compounds of the general formula (IV)

Hal—R³ (IV)

in which

R³ has the abovementioned meaning and Hal represents halogen, preferably chlorine, bromine or iodine, in inert solvents, in the presence of bases, if appropriate in the presence of reaction accelerators, then converting, if appropriate, functional groups into other functional groups by reduction, hydrolysis, oxidation or reaction with electrophilic reagents, and then, in the case of the preparation of the salts, reacting with appropriate acids, or by

[B] reacting monosubstituted basic 2-aminotetralins of the general formula (Ic)

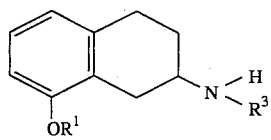 (Ic)

in which

R¹ and R³ have the abovementioned meaning, with compounds of the general formula (V)

D—R²' (V)

in which

R²' has the abovementioned meaning and

D represents a carbonyl oxygen, in inert solvents, if appropriate in the presence of a catalyst, then reducing the intermediates obtained in inert solvents, then converting, if appropriate, functional groups into other functional groups by reduction, hydrolysis, oxidation or reaction with electrophilic reagents, and then, in the case of the preparation of the salts, reacting with appropriate acids.

Depending on the type of the starting compounds used, both process versions A and B can be described by the following equations:

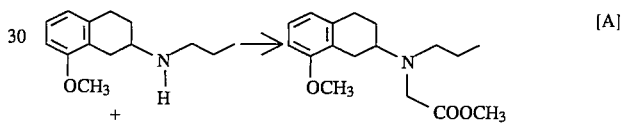 [A]

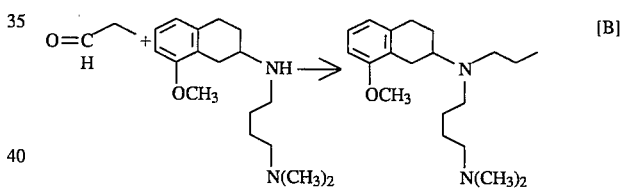 [B]

Process version A:

Those conventional organic solvents which do not change under the reaction conditions can be used here as solvents. These preferably include alcohols such as methanol, ethanol, propanol or isopropanol, or ethers such as diethyl ether, dioxane, tetrahydrofuran, glycol dimethyl ether or butyl methyl ether, or ketones such as acetone or butanone, or amides such as dimethylformamide or hexamethylphosphoric triamide, or dimethyl sulphoxide, acetonitrile or ethyl acetate, or halogenated hydrocarbons such as methylene chloride, chloroform or carbon tetrachloride, or pyridine, picoline or N-methylpiperidine. Mixtures of the solvents mentioned can likewise be used.

Suitable bases are the conventional inorganic or organic bases. These preferably include alkali metal hydroxides such as, for example, sodium or potassium hydroxide, or alkali metal carbonates such as sodium or potassium carbonate, or alkali metal alcoholates such as, for example, sodium or potassium methanolate, or sodium or potassium ethanolate, or organic amines such as triethylamine, picoline or N-methylpiperidine, or amides such as sodium amide or lithium diisopropylamide, or organometallic compounds such as butyllithium or phenyllithium.

In general, the reaction is carried out in a temperature range from 0° C. to +150° C., preferably from room temperature to +80° C.

In general, the reaction is carried out at atmospheric pressure. However, it is also possible to carry out the reaction at increased or reduced pressure.

As reaction accelerators, alkali metal iodides, preferably sodium iodide or potassium iodide, are employed in general.

In this reaction, the base is employed in an amount from 1 to 5, preferably from 1 to 2, mols, relative to 1 mol of the halogen compound, The halogen compound is preferably employed in an excess amount of up to 10-fold, preferably in an excess amount of up to 5-fold, to the alkyl-substituted 2-aminotetralin (Ib).

Process version B:

In the case of the reaction with primary amines the intermediates are Schiff bases, and in the case of the reaction with secondary amines the intermediates are enamines or immonium salts.

The intermediates in the first step are prepared in inert organic solvents, if appropriate in the presence of a catalyst and if appropriate in the presence of a dehydrating agent.

The process according to the invention may be carried out in 2 steps, i.e. with isolation of the intermediates. It is also possible to carry out the reduction as a one-pot process.

Suitable inert solvents in this reaction are those conventional organic solvents which do not change under the reaction conditions. These preferably include alcohols such as methanol, ethanol, propanol or isopropanol, or ethers such as diethyl ether, butyl methyl ether, dioxane, tetrahydrofuran, glycol dimethyl ether or diethylene glycol diethyl ether, or halogenated hydrocarbons such as, for example, methylene chloride, chloroform or carbon tetrachloride, or hydrocarbons such as benzene, toluene, xylene, or petroleum fractions, or amides such as dimethylformamide or hexamethylphosphoric triamide, or acetic acid. In addition, it is possible to use mixtures of the solvents mentioned.

In general, protonic acids are used as catalysts. These preferably include inorganic acids such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or having aryl radicals, such as, for example, methanesulphonic acid, ethanesulphonic acid, benzenesulphonic acid or toluenesulphonic acid.

The water formed during the reaction may be removed, if appropriate, as a mixture with the solvent used, during or after the reaction, for example by distillation or by addition of dehydrating agents, such as, for example, phosphorus pentoxide, or preferably by molecular sieve.

In general, the reaction is carried out in a temperature range from 0° C. to +150° C., preferably from +20° C. to +100° C.

In the case of removal of the water formed during the reaction by azeotropic distillation with the solvents used, the reaction is preferably carried out at the boiling temperature of the azeotrope.

The reaction can be carried out at atmospheric, increased and at reduced pressure (e.g. 0.5–5 bar). In general, the reaction is carried out at atmospheric pressure.

When carrying out the reaction, the compound (V) is employed in an amount from 0.1–10, preferably from 0.5–5 mols, relative to 1 mol of monosubstituted basic 2-aminotetralin (Ic).

The intermediates are reduced either by hydrogen in water or in inert organic solvents such as alcohols, ethers or halogenated hydrocarbons, or mixtures thereof, using catalysts such as Raney nickel, palladium, palladium on animal charcoal, or platinum, or using hydrides in inert solvents, if appropriate in the presence of a catalyst.

The reaction is preferably carried out using hydrides, such as complex borohydrides or aluminium hydrides. Sodium borohydride, lithium aluminum hydride or sodium cyanoborohydride are particularly preferably employed here.

Suitable solvents in this reaction are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether or amides such as hexamethylphosphoric triamide or dimethylformamide, or acetic acid. It is also possible to use mixtures of the solvents mentioned.

In general, protonic acids are used as catalysts during the reduction. These preferably include inorganic acids such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or having aryl radicals, such as, for example, methanesulphonic acid, ethanesulphonic acid, benzenesulphonic acid or toluenesulphonic acid.

When carrying out the process according to the invention, it has proved favorable to carry out the reaction of the compounds (V) with the amines (Ic) in an inert solvent, preferably in acetic acid or alcohols such as, for example, methanol, ethanol, propanol or isopropanol, or mixtures thereof, in the presence of inorganic or organic acids, such as, for example, hydrochloric acid or acetic acid, and in the presence of a reducing agent, preferably complex hydrides such as, for example, sodium borohydride or sodium cyanoborohydride, if appropriate in the presence of a dehydrating agent, preferably molecular sieve, as a one-pot process.

In this case, the reaction is carried out in temperature range from 0° C. to +150° C., preferably from 0° C. to +100° C., at atmospheric pressure. It is also possible to carry out the reaction at reduced pressure or at increased pressure (e.g. in a Carius tube).

If the process according to the invention is carried out as a one-pot reaction, it has proved favourable to employ the aminotetralin (Ic) in an amount from 0.1 to 10, preferably 0.5 to 5 mols, relative to 1 mol of the compound (V).

The conversion of functional groups into other functional groups in the preparation process described above is carried out, depending on the type of the functional groups, by oxidation, reduction, hydrolysis or by reaction with electrophilic reagents and will be described below.

1. In general, the nitrile group is reduced to the amino group using metal hydrides, preferably using lithium aluminum hydride, aluminum hydride (prepared, for example, by reaction of lithium aluminum hydride with 100% strength sulphuric acid or with aluminum chloride), or mixtures thereof, in inert solvents such as ethers or chlorinated hydrocarbons, preferably ethers such as, for example, tetrahydrofuran, diethyl ether or dioxane, in a temperature range from –20° C. to +100° C., preferably from 0° C. to +50° C., at atmospheric pressure.

In addition, the reduction is possible by hydrogenation of the nitriles in inert solvents such as alcohols, for example methanol, ethanol, propanol or isopropanol, in the presence of a noble metal catalyst such as platinum, palladium, palladium on animal charcoal, or Raney nickel, in a temperature range from 0° C. to +150° C., preferably from room temperature to +100° C., at atmospheric pressure or at increased pressure.

The reaction may be illustrated by the following equation:

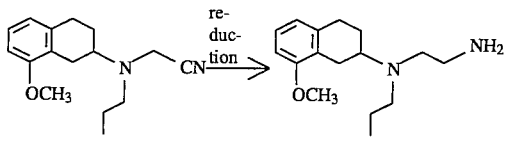

2. In general, carbamates are converted to N-methylamines by reduction using hydrides, preferably using lithium aluminum hydride, in inert solvents such as ethers, hydrocarbons or chlorinated hydrocarbons, preferably in ethers, such as, for example, diethyl ether, tetrahydrofuran or dioxane, in a temperature range from 0° C. to +150° C., preferably from +20° C. to +100° C., at atmospheric pressure.

The reaction may be illustrated by the following equation:

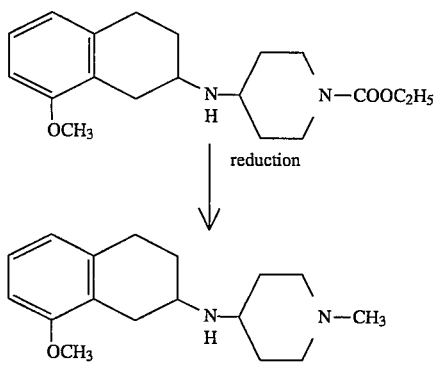

3. In general, alkoxycarbonyl groups are reduced to alcohol groups using hydrides, preferably using lithium aluminum hydride in inert solvents such as ethers, hydrocarbons or halogenated hydrocarbons, or mixtures thereof, preferably in ethers, such as, for example, diethyl ether, tetrahydrofuran or dioxane, in a temperature range from 0° C. to +150° C., preferably from +20° C. to +100° C., at atmospheric pressure.

The reaction may be illustrated by the following equation

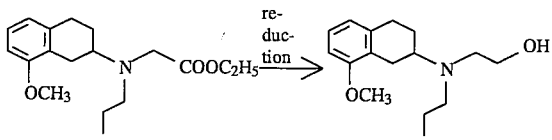

4. In general, the nitrile group is hydrolyzed to the carboxamide group using strong mineral acids, preferably using hydrochloric acid, in inert solvents such as water and/or alcohols, such as, for example, methanol, ethanol, propanol or isopropanol, in a temperature range from 0° C. to +150° C., preferably from +20° C. to +100° C., at atmospheric pressure.

The reaction may be described by the following equation:

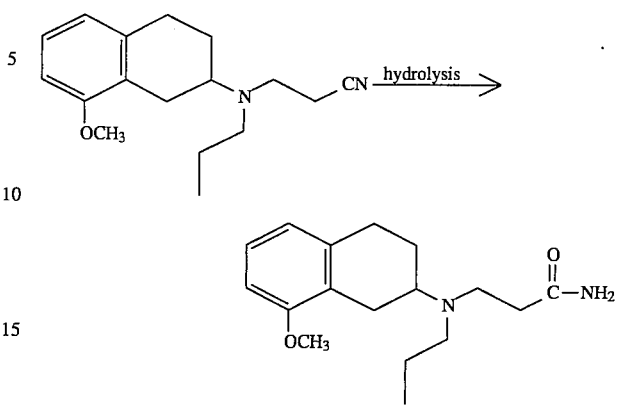

5. A large number of further compounds according to the invention are obtained by reacting NH- or OH-acidic compounds ($R^4$=OH or $NR^5R^6$, where $R^5$=H and $R^6$=H, alkyl, aryl or aralkyl) with electrophilic reagents:

a) In general, amines are converted to carboxamides by reaction with carboxylates in inert solvents such as ethers or their mixtures, or hydrocarbons, preferably in furan, such as, for example, diethyl ether, tetrahydrofuran or dioxane, if appropriate in the presence of bases such as alkali metals, alkali metal hydrides, alkali metal alcoholates or organolithium compounds, preferably in the presence of alkali metals such as, for example, sodium, or alkali metal hydrides such as sodium hydride or potassium hydride, in a temperature range from +20° C. to +150° C., preferably at the boiling temperature of the solvent used, at atmospheric pressure.

In addition, it is possible to prepare the amides using carboxylic acid halides or anhydrides, preferably using carboxylic acid chlorides, in inert solvents such as ethers, hydrocarbons or halogenated hydrocarbons, or mixtures thereof, preferably in ethers, such as, for example, diethyl ether or tetrahydrofuran, or halogenated hydrocarbons such as methylene chloride or chloroform, if appropriate in the presence of bases such as alkali metal carbonates, for example sodium carbonate or potassium carbonate, or organic amines such as, for example, triethylamine or pyridine, in a temperature range from −20° C. to +100° C., preferably from 0° C. to +60° C., at atmospheric pressure.

The reaction may be illustrated by the following equation:

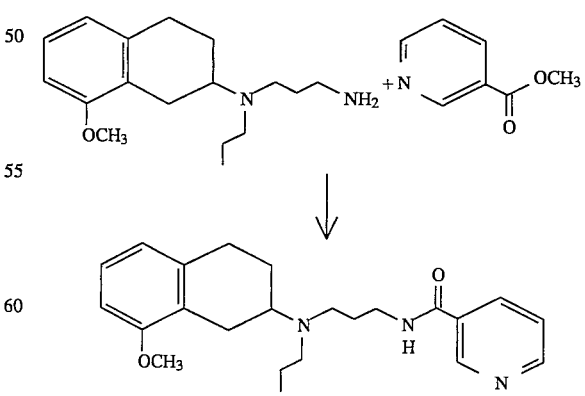

b) In general, amines are converted to carbamates using carbonic acid derivatives, such as carbonates or carbonyl halides, preferably using asymmetrical carbonates, particularly preferably using carbonates which carry one phenyl ester radical, or using carbonyl chlorides, in inert solvents such as ethers, hydrocarbons or halogenated hydrocarbons, or mixtures thereof, preferably in ethers such as, for example, diethyl ether, tetrahydrofuran or dioxan, in a temperature range from +20° C. to +150° C., preferably from +20° C. to +100° C., at atmospheric pressure.

The reaction may be described by the following equation:

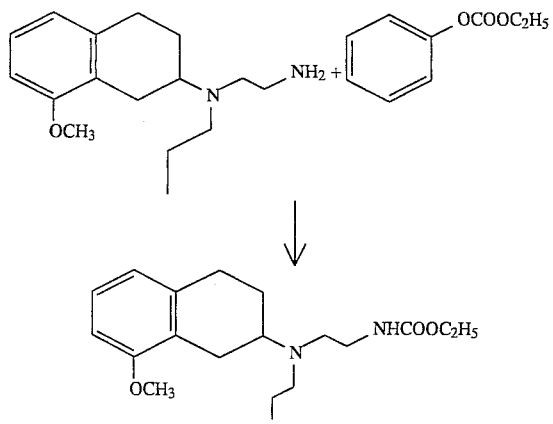

c) In general, amines are converted to ureas by reaction with isocyanates in inert solvents such as ethers, hydrocarbons or halogenated hydrocarbons or mixtures thereof, preferably in ethers such as, for example, diethyl ether or tetrahydrofuran, or in halogenated hydrocarbons such as, for example, methylene chloride or chloroform, in a temperature range from −20° C. to +150° C., preferably from 0° C. to +100° C., at atmospheric pressure.

The reaction may be described by the following equation:

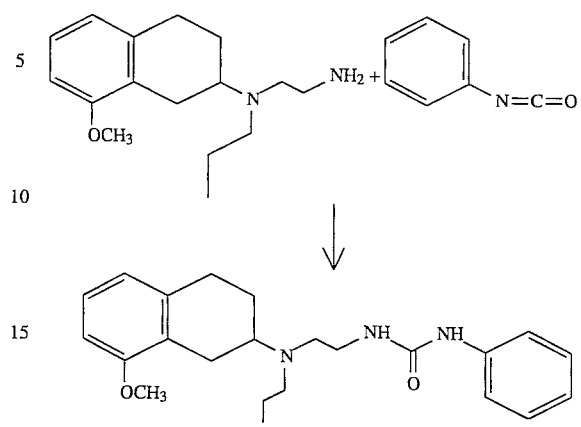

d) In general, amides are converted to sulphonamides or aminosulphamoyl derivatives using sulphonyl halides or using amidosulphonyl halides, preferably using the corresponding chlorides, in inert solvents such as ethers, hydrocarbons or halogenated hydrocarbons, or mixtures thereof, preferably in halogenated hydrocarbons such as, for example, methylene chloride or chloroform, if appropriate in the presence of bases such as alkali metal hydroxides, alkali metal carbonates, alkali metal alcoholates or organic amines, preferably using alkali metal hydroxides such as sodium hydroxide or potassium hydroxide, alkali metal carbonates such as, for example, sodium carbonate or potassium carbonate, or organic amines such as triethylamine or pyridine, in a temperature range from −20° C. to +100° C., preferably from 0° C. to +50° C., at atmospheric pressure The reaction may be illustrated by the following equation:

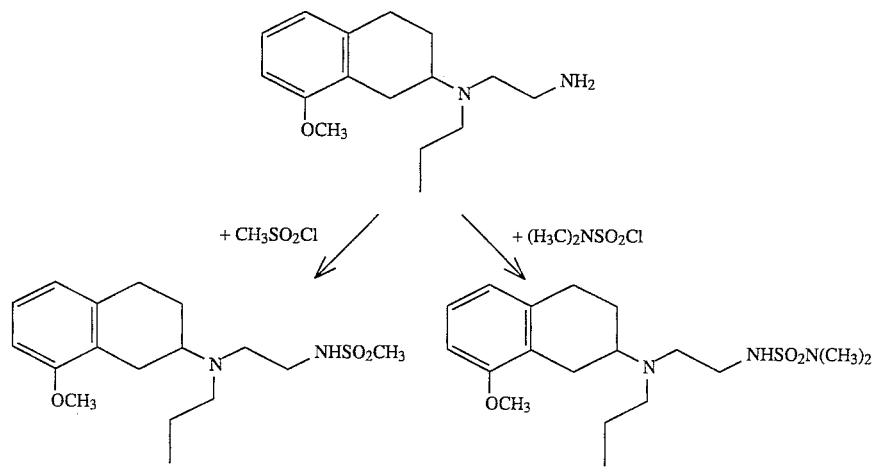

e) In general, the hydroxyl group is converted to a carbonate by reaction with halogenoformates, preferably with chloroformates, in inert solvents such as ethers, hydrocarbons or halogenated hydrocarbons, preferably in halogenated hydrocarbons such as methylene chloride or chloroform, or in ethers such as diethyl ether or tetrahydrofuran, if appropriate in the presence of bases such as alkali metal hydroxides, alkali metal carbonates or organic amines, preferably in the presence of organic amines such as triethylamine, pyridine, picoline or dimethylaminopyridine, in a temperature range from −20° C. to +100° C., preferably from 0° C. to +30° C., at atmospheric pressure.

The reaction may be illustrated by the following equation:

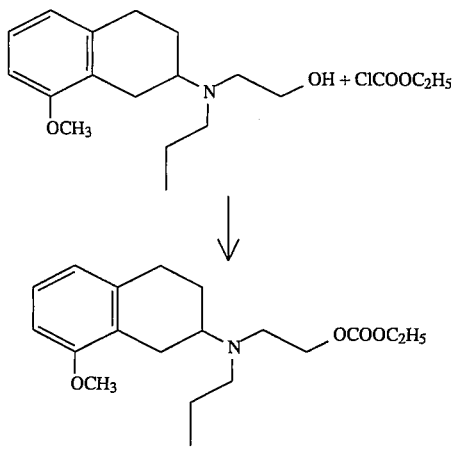

f) In general, cyclic sulphonamides are prepared by reaction of intramolecular electrophiles in inert dipolar aprotic solvents, preferably in dimethylformamide, hexamethylphosphoric triamide or dimethyl sulphoxide, if appropriate in the presence of bases such as alkali metals, alkali metal hydrides, alkali metal amides, alkali metal alcoholates or organolithium compounds, preferably in the presence of alkali metal hydrides such as sodium hydride or potassium hydride, or alkali metal amides such as sodium amide or lithium diisopropylamide, if appropriate in the presence of catalytic amounts of an alkali metal iodide, for example sodium iodide or potassium iodide, in a temperature range from −20° C. to +100° C., preferably from 0° C. to +50° C., at atmospheric pressure.

The reaction may be illustrated by the following equation:

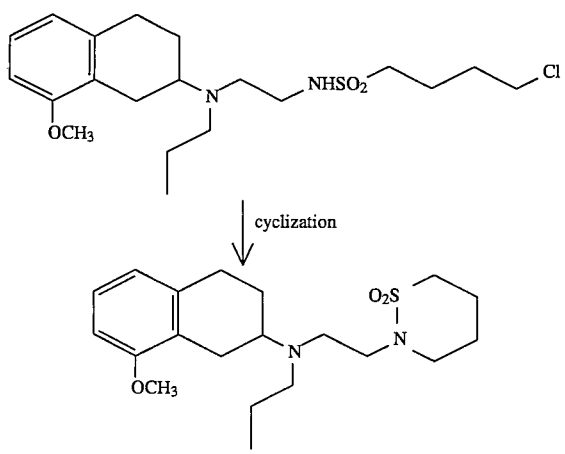

5. In general, the thioether group is oxidized to sulphoxides or sulphones using oxidants such as peroxo compounds or hydrogen peroxide itself, preferably using hydrogen peroxide, in inert solvents such as carboxylic acids and carboxylic acid anhydrides, preferably in acetic acid, in a temperature range from −20° C. to +100° C., preferably from 0° C. to +50° C.

The reaction may be illustrated by the following equation:

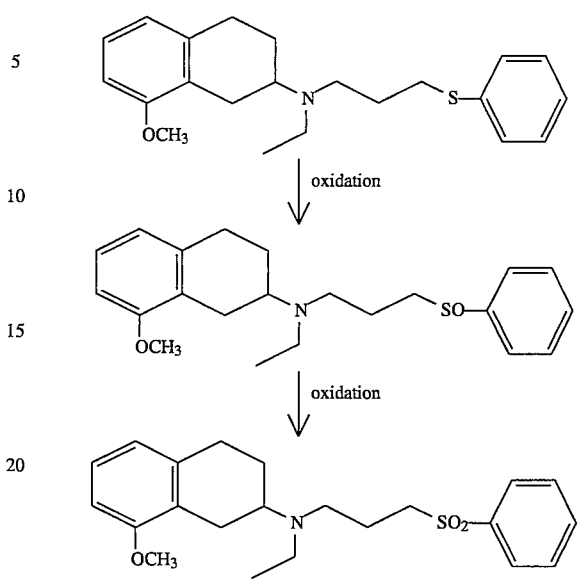

In addition to varying the functional groups in $R^3$, 8-hydroxy-substituted 2-aminotetralins ($R^1$=H) are accessible from the corresponding 8-methoxy-substituted compounds ($R^1$=CH$_3$) by known dealkylation methods [T. Green, Protective Groups in Organic Chemistry, page 89, 1st edition, J. Wiley & Sons, New York, 1981]. Expediently, those methods are used in each case which are compatible with the nature of the radical $R^4$.

In addition, it is possible to prepare disubstituted 2-aminotetralins (Ia) in which $R^1$ and $R^2$ have the abovementioned meaning and $R^3$ represents a 2-cyanoethyl group, by reacting alkyl-substituted 2-aminotetralins (Ib) with acrylonitrile, if appropriate in the presence of a catalyst, in particular copper acetate.

In addition, it is possible to introduce the radical $R^3$ by a Mannich reaction (by reacting alkyl-substituted 2-aminotetralins (Ib) with formaldehyde and CH-acidic compounds, in particular having acetylene groups).

The following may be used according to the invention, for example, as tetralones: 8-Hydroxytetralone and 8-methoxytetralone.

The amines of the general formula (III) employed as starting compounds are known or can be prepared by known methods [Houben-Weyl's "Methoden der organischen Chemie" (Methods of Organic Chemistry), vol. XI/1 and XI/2].

The following may be used according to the invention, for example, as amines: methylamine, ethylamine, propylamine, isopropylamine, butylamine, 4-dimethylaminobutylamine, 4-diethylaminobutylamine, 3-dimethylaminopropylamine, 3-diethylaminopropylamine, 2-dimethylaminoethylamine, 2-diethylaminoethylamine, 2-amino-1-ethoxycarbonylamido-ethane, 3-amino-1-ethoxycarbonylamido-propane, 4-amino-1-ethoxycarbonylamido-butane, 3-aminoquinuclidine, 2-[(phenylaminocarbonyl)amino]ethylamine, 2-[(phenylaminocarbonyl)amino]propylamine, 4-aminomethylpiperidine, 4-(ethoxycarbonyl)aminoethyl-piperidine, N-methylpiperazine, 4-amino-1-carboxyethyl-piperidine, N,N-dimethylpropylidene-diamine, N,N-diethylpropylidene-diamine, N,N-diethylethylidene-diamine, N,N-dimethylethylene-diamine, N-(2-aminoethyl)ethylcarbamate and N-(2-aminoethyl)propylcarbamate.

The halogen compounds of the general formula (IV) are known or can be prepared by known methods [Boilstein's Handbuch der organischen Chemie (Beilstein's Handbook of Organic Chemistry) 2, 197, 201, 250, 278; 3, 9, 10; 21, 461, 462, 463].

The following may be used according to the invention, for example, as halogen compounds: chloroacetonitrile, 2-chloropropionitrile, 3-chlorobutyronitrile, 3-bromopropylphthalimide, 3-chloropropylphthalimide, 2-bromoethylphthalimide, 2-bromoethylphthalimide, 4-bromobutylphthalimide, 4-chlorobutylphthalimide, chloroacetic diethylamide, chloroacetic dimethylamide, methyl chloroacetate, ethyl chloroacetate, ethyl bromoacetate, methyl bromoacetate, 2-γ-bromobutyl-1,2-benzoisothiazol-3(2H)-one 1,1-dioxide and 2-γ-bromopropyl-1,2-benzoisothiazol-3(2H)-one 1,1-dioxide.

The carbonyl compounds of the general formula (V) employed as starting compounds are known or can be prepared by known methods [Beilstein's Handbuch der organischen Chemie (Bellstein's Handbook of Organic Chemistry) 1, 594, 629, 662].

The following may be used according to the invention, for example, as ketone compounds: acetaldehyde, propionaldehyde and butyraldehyde;

The substances of the general formula (I) according to the invention have a high affinity for cerebral 5-hydroxytryptamine receptors of the 5-HT$_1$ type. This affinity of the compounds according to the invention is increased compared to those known from the prior art (EP-A1-41 488). Agonistic, partially agonistic or antagonistic actions on the serotonin receptor are connected with this, against which the known substances have purely agonistic properties.

The high-affinity ligands, described in the present invention, for the serotonin-1 receptor thus represent better active compounds for combating diseases which are characterized by disturbances to the serotoninergic system, particularly when involving receptors which have a high affinity to 5-hydroxytryptamine (5-HT$_1$ type). They are therefore suitable for the treatment of diseases of the central nervous system, such as anxiety, tension and depression, sexual dysfunctions caused by the central nervous system, and insomnia. The substances according to the invention are furthermore suitable for treatment of cognitive deficits, as arise, for example, in senile dementia and in Alzheimer's disease, and other brain-function disturbances. In addition, these active compounds are also suitable for modulation of the cardiovascular system. They also engage in the regulation of the cerebral blood supply, and thus represent effective agents for combating migraine. The compounds according to the invention can likewise be employed for combating pain. They are also suitable for combating diseases of the intestinal tract, which are characterized by disturbances of the serotoninergic system.

The new active compounds can be converted in a known manner into the customary formulations, such as tablets, dragees, pills, granules, aerosols, syrups, emulsions, suspensions and solutions, using inert non-toxic, pharmaceutically suitable excipients or solvents. The therapeutically active compound should in each case be present here in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example, when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol), excipients, such as, for example, ground natural minerals (for example kaolins, aluminas, talc and chalk), ground synthetic minerals (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersants (for example lignin, sulphite waste liquors, methylcellulose, starch and polyvinylpyrrolidone) and lubricants (for example magnesium stearate, talc, stearic acid and sodium sulphate).

Administration is effected in the customary manner, preferably orally or parenterally, particularly perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl sulphate and talc, can be used concomitantly when making tablets. In the case of aqueous suspensions, the active compounds can be mixed with various flavor-improving agents or colorants in addition to the abovementioned auxiliary substances.

In the case of parenteral use, solutions of the active compounds, using suitable liquid excipients, can be employed.

In general, it has proved advantageous, in the case of intravenous administration, to administer amounts of about 0.001 to 1 mg/kg, preferably about 0.01 to 0.5 mg/kg, of body weight to achieve effective results, and in the case of oral administration, the dosage is about 0.01 to 20 mg/kg, preferably 0.1 to 10 mg/kg of body weight.

Nevertheless, it may be necessary, under certain circumstances, to deviate from the amounts mentioned, and in particular to do so as a function of the body weight or of the nature of the administration method, of the individual behavior towards the medicament, the nature of its formulation, and the time or interval over which the administration takes place. Thus, it can in some cases be sufficient to manage with less than the abovementioned minimum amount, whereas in other cases the upper limit mentioned must be exceeded. In the case of administration of larger amounts, it may be advisable to divide these into several individual administrations over the course of the day.

PREPARATION EXAMPLES

The respective $R_f$ values listed were—if not otherwise noted—determined by thin layer chromatography on silica gel (alumincan foil, silica gel 60 F 254, E. Merck). The substance spot was visualized by observation under UV light and/or by spraying with 1% strength potassium permanganate solution.

The flash chromatography was carried out on silica gel 60, 0.040–0.063 mm, E. Merck (see Still et al., J. Org. Chem. 43, 2923, 1978; for simpler separation problems, see Aldrichimica Acta 18, 25, 1985). Elution with solvent gradients means: starting with the pure, nonpolar solvent mixture component, the polar eluant component is admixed to an increasing extent, until the product desired is eluted (TLC check).

In the case of all products, the solvent was removed at

Example 1

2-[4-Ethoxycarbonylamino-methyl)piperidin-1-yl]-8-methoxy-1,2,3,4-tetrahydronaphthalene

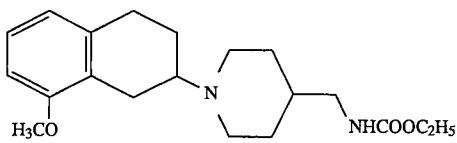

The solution of 1.70 g (9.0 mmol) of 4-(ethoxycarbonylamino-methyl)-piperidine (obtained from 4-aminomethylpiperidine and diethyl carbonate in the presence of 4-dimethylaminopyridine) in 18 ml of methanol was treated with 9.0 ml (9.0 mmol) of 1N methanolic hydrochloric acid. After addition of 0.53 g (3.0 mmol) of 8-methoxy-2-tetralone, the mixture was stirred for a further 5 minutes. 0.20 g (3.3 mmol) of sodium cyanoborohydride was then added and the mixture was stirred for 15 hours at room temperature, followed by standing for 18 days at about +4° C.

The reaction mixture was substantially concentrated in a rotary evaporator, taken up in tert.-butyl methyl ether and stirred vigorously for 30 minutes with dilute sodium hydroxide solution (pH of the aqueous phase was adjusted to 10). The aqueous phase was extracted carefully with tert.-butyl methyl ether. Washing the combined organic phases with water and saturated sodium chloride solution, drying over magnesium sulphate, and concentrating in a rotary evaporator yielded the crude product as an oil.

0.45 g (43%) of the title compound could be obtained as a yellowish syrup by chromatography on silica gel (toluene/ethanol gradients).

$R_f$ (toluene/methanol 4:1): 0.38 IR (chloroform): 3460, 3003, 2920, 1681, 1587.

Example 2

2-[4-(Ethoxycarbonylamino-methyl)piperidin-1-yl]-8-methoxy-1,2,3,4-tetrahydronaphthalene hydrochloride The hydrochloride of the compound from Example 1 was obtained by treatment with ethereal hydrochloric acid.

Melting point: 85° C., vitrification, 105°–110° C., with decomposition.

Example 3

8-Methoxy-2-(4-methylpiperazin-1-yl)-1,2,3,4-tetrahydronaphthalene

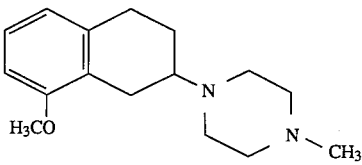

1.76 g (10 mmol) of 8-methoxy-2-tetralone, 3.00 g (30 mmol) of N-methylpiperazine and 1.80 g (30 mmol) of glacial acetic acid were refluxed in 30 ml of methanol for 4 hours. 1.30 g (20 mmol) of sodium cyanoborohydride were then added, and the mixture was refluxed for a further hour. The reaction mixture was substantially concentrated in a rotary evaporator, taken up in tert.-butyl methyl ether, and stirred vigorously for 30 minutes in 20% strength sodium hydroxide solution. The aqueous phase was extracted carefully with tert.-butyl methyl ether. Washing the combined organic phases with water and saturated sodium chloride solution, drying over potassium carbonate, and concentrating in a rotary evaporator yielded the crude product as an oil (2.9 g). This crude product was combined with that obtained from a batch of equal size (this reaction was carried out in the presence of 3A molecular sieve, otherwise the same) and chromatographed on silica gel (toluene/methanol 4:1). 4.20 g of the title compound were obtained in this fashion as a brownish oil (80%).

$R_f$ (chloroform/methanol 2:1): 0.61

Example 4

8-Methoxy-2-(4-methylpiperazin-1-yl)-1,2,3,4-tetrahydronaphthalene dihydrochloride The dihydrochloride was obtained as a virtually colorless solid from the compound of Example 3 using ethereal hydrochloric acid.

Melting point: >265° C. Analysis ($C_{16}H_{24}N_2O \times 2HCl \times 0.5 H_2O$) Calc. C 56.1 H 7.9 N 8.2 Cl 20.7 Found C 56.0 H 7.9 N 8.1 Cl 20.6

Example 5

2-(1-Ethoxycarbonylpiperidin-4-yl)amino-8-methoxy-1,2,3,4-tetrahydronaphthalene

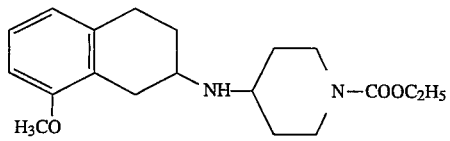

The solution of 2.00 g (11.4 mmol) of 8-methoxy-2-tetralone, 2.90 g (17 mmol) of 4-amino-1-ethoxycarbonylpiperidine and 3.40 g (57 mmol) of glacial acetic acid in 80 ml of methanol was stirred at 0° C. for 30 minutes. After addition of 3.85 g (45.6 mmol) of sodium cyanoborohydride, the mixture was stirred for 3 hours at room temperature. The reaction mixture was substantially concentrated, taken up in toluene, reconcentrated, treated with tert.-butyl methyl ether, and stirred vigorously for 30 minutes with dilute sodium hydroxide solution (pH of the aqueous phase adjusted to 10). The aqueous phase was extracted carefully with tert.-butyl methyl ether. Washing the combined organic phases with water and saturated sodium chloride solution, drying over potassium carbonate, and concentrating in a rotary evaporator yielded the crude product as an oil.

After chromatography on silica gel (toluene/ethyl acetate gradients with addition of 0.5% of triethylamine), 2.10 g (55%) of the title compound were obtained.

$R_f$ (toluene/methanol 4:1): 0.26 IR (chloroform): 3005, 2931, 1679, 1587.

Example 6

2-(1-Ethoxycarbonylpiperidin-4-yl)amino-8-methoxy-1,2,3,4-tetrahydronaphthalene hydrochloride The hydrochloride, producible from the compound of Example 5 by treatment with ethereal hydrochloric acid, precipitated as a colorless solid.

Melting point: >270° C. Analysis ($C_{19}H_{28}N_2O_3 \times HCl$) Calc.: C 61.9 H 7.9 N 7.6 Cl 9.6 Found: C 61.3 H 8.0 N 7.6 Cl 9.4

Example 7

2-(3-Dimethylaminopropyl)amino-8-methoxy-1,2,3,4-tetrahydronaphthalene

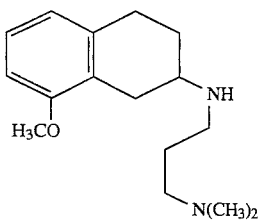

The solution of 7.04 g (40 mmol) of 8-methoxy-2-tetralone, 6.12 g (60 mmol) of 3-dimethylamino-1-propylamine and 18 g (300 mmol) of glacial acetic acid was stirred at 0° C. for 30 minutes. After addition of 10.0 g (160 mmol) of sodium cyanoborohydride, the mixture was stirred for 3 hours at room temperature.

The reaction mixture was substantially concentrated in a rotary evaporator, taken up in tert.-butyl methyl ether, and stirred vigorously for 30 minutes with 20% strength sodium hydroxide solution. The aqueous phase was extracted carefully with tert.-butyl methyl ether. Washing the combined organic phases with water and saturated sodium chloride solution, drying over potassium carbonate, and concentrating in a rotary evaporator yielded the crude product as an oil. The crude product was purified by chromatography on silica gel (chloroform/methanol gradients with addition of 1% of triethylamine). 5.10 g (49%) of the title compound were obtained in this fashion as a brown oil.

$R_f$ (chloroform/methanol/triethylamine 20:10:0.1): 0.1 IR (chloroform): 3666, 3006, 1587, 1470.

Example 8

2-(3-Dimethylaminopropyl)amino-8-methoxy-1,2,3,4-tetrahydronaphthalene dihydrochloride The dihydrochloride of the compound of Example 7 could be obtained, in the form of pale gray crystals, using ethereal hydrochloric acid.

Melting point: 173°–178° C.

Example 9

2-(2-Diethylaminoethyl)amino-8-methoxy-1,2,3,4-tetrahydronaphthalene

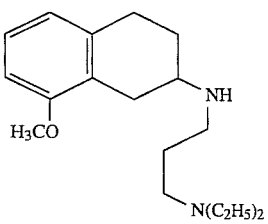

3.50 g (20 mmol) of 8-methoxy-2-tetralone, 4.60 g of 2-diethylamino-1-ethylamine and 4.80 g (80 mmol) of glacial acetic acid in 150 ml of methanol were stirred at 0° C. for 30 minutes. After addition of 5.00 g of sodium cyanoborohydride, the mixture was allowed to stand at room temperature for 15 hours.

The reaction mixture was substantially concentrated in a rotary evaporator, taken up in tert.-butyl methyl ether, and stirred vigorously for 30 minutes with 20% strength sodium hydroxide solution. The aqueous phase was extracted carefully with tert.-butyl methyl ether. Washing the combined organic phases with water and saturated sodium chloride solution, drying over potassium carbonate and concentrating in a rotary evaporator yielded the crude product as an oil. Chromatography on silica gel (toluene/ethanol gradients) supplied 3.80 g (69%) of the title compound as a syrup.

$R_f$ (chloroform/methanol) 2:1): 0.18 IR (chloroform, $CHCl_3$): 3282, 2970, 1586, 1470.

Example 10

2-(2-Diethylaminoethyl)amino-8-methoxy-1,2,3,4-tetrahydronaphthalene hydrochloride The dihydrochloride, obtained from the compound of Example 9 by treatment with ethereal hydrochloric acid in ether, precipitated as a beige solid.

Melting point: 60° C., vitrification, about 100° C., decomposition

Example 11

2-(2-Ethoxycarbonylamino-ethyl)amino-8-methoxy-1,2,3,4-tetrahydronaphthalene

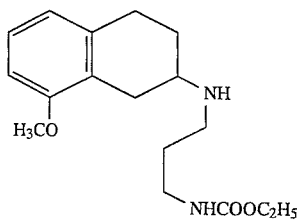

10.0 g (159 mmol) of sodium cyanoborohydride were added to the solution of 7.00 g (40 mmol) of 8-methoxy-2-tetralone, 8.00 g (61 mmol) of N-(2-aminoethyl)ethylcarbamate and 9.60 g (160 mmol) of glacial acetic acid at 0° C. After 15 hours at room temperature, the mixture was concentrated, taken up in tert.-butyl methyl ether, and treated with water. The pH of the aqueous phase was adjusted to 10 using sodium hydroxide solution. The mixture was stirred vigorously for 30 minutes. The organic phase was separated off, and the aqueous phase was extracted thoroughly with the last-mentioned solvent. Drying the organic phase and concentrating supplied an oil, which was purified by chromatography on silica gel (toluene/ethanol gradients with addition of 0.3% triethylamine). 5.40 g (46%) of the pure title compound were obtained as a brownish oil.

A further 6.00 g of the desired product were eluted, together with relatively small amounts of relatively polar impurities (this fraction was of adequate purity for further reactions).

$R_f$ (toluene/methanol 4:1): 0.17

Example 12

2-(2-Ethoxycarbonylamino-ethyl)amino-8-methoxy-1,2,3,4-tetrahydronaphthalene hydrochloride The hydrochloride was obtained from the pure product of Example 11 using ethereal hydrochloric acid.

Melting point: 80° C. (with decomposition)

Example 13

2-[N-(3-Dimethylaminopropyl)-N-propionyl]amino-8-methoxy-1,2,3,4-tetrahydronaphthalene

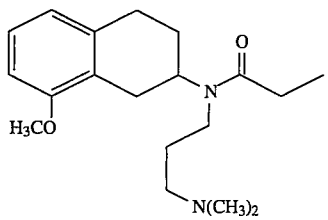

3.3 g (25 mmol) of propionic anhydride and 22 ml 3N sodium hydroxide solution were added to the mixture of 1.30 g (5 mmol) of 2-(3-dimethylaminopropyl)amino-8-methoxy-1,2,3,4-tetrahydronaphthalene in 35 ml of ether and 7 ml of water at 0° C. After stirring vigorously for 1 hour, the same amount of propionic anhydride, and also 16 ml of 3N sodium hydroxide solution, were added again. After a further hour, a further 2.5 g of propionic anhydride and 12 ml of 3N sodium hydroxide solution were added. After stirring for 15 hours at room temperature, the organic phase was separated off. The aqueous phase was extracted twice with ether. The combined organic extracts were washed with saturated sodium chloride solution, dried over magnesium sulphate, and freed of solvent in vacuo. 1.20 g (75%) of the free base were thus obtained as a clear oil.

$R_f$ (toluene/methanol 4:1): 0.22 IR (chloroform): 2981, 1626, 1588, 1469 MS: 318, 217, 190, 160.

Example 14

2-[N-(3-Dimethylaminopropyl)-N-propionyl]amino-8-methoxy-1,2,3,4-tetrahydronaphthalene hydrochloride The hydrochloride of the compound from Example 13 could be obtained as a foam using ethereal hydrochloric acid.

Analysis ($C_{19}H_{30}N_2O_2 \times HCl \times H_2O$): Calc.: C 61.2 H 8.9 N 7.5 Found: C 61.5 H 8.9 N 7.5

Example 15

2-[N-(2-Diethylaminoethyl)-N-acetyl]amino-8-methoxy-1,2,3,4-tetrahydronaphthalene

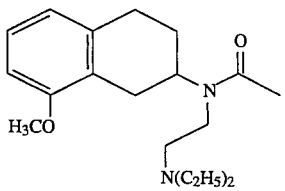

2.2 g (22 mmol) of acetic anhydride and 20 ml of 3N sodium hydroxide solution were added to the mixture of 1.20 g (4.3 mmol) of 2-(2-diethylaminoethyl)amino-8-methoxy-1,2,3,4-tetrahydronaphthalene in 35 ml of ether and 7 ml of water at 0° C. After stirring vigorously for 1 hour the same amount of acetic anhydride, and also 15 ml of 3N sodium hydroxide solution, were added again. After a further hour, a further 1.6 g of acetic anhydride and 12 ml of 3N sodium hydroxide solution were added. After stirring for 15 hours at room temperature, the organic phase was separated off. The aqueous phase was extracted twice with ether. The combined organic extracts were washed with saturated sodium chloride solution, dried over magnesium sulphate, and freed of solvent in vacuo. The crude product thus obtained was purified by chromatography on silica gel (toluene/ethyl acetate gradients). This supplied 0.50 g (37%) of the title compound as a yellow oil.

$R_f$ (toluene/methanol 4:1): 0.22 IR (chloroform): 3002, 2970, 1625, 1588, 1470 MS: 318, 246, 161.

Example 16

2-[N-(2-Diethylaminoethyl)-N-acetyl]amino-8-methoxy-1,2,3,4-tetrahydronaphthalene hydrochloride The hydrochloride of the compound from Example 15 could be precipitated as a colorless solid in ether using ethereal hydrochloric acid.

Melting point: about 100° C., vitrification, about 150° C., with decomposition Analysis ($C_{19}H_{30}N_2O_2 \times HCl$) Calc.: C 64.3 H 8.8 N 7.9 Found: C 63.9 H 8.8 N 7.9

Example 17

2-[N-(3-Dimethylaminopropyl)-N-propyl]amino-8-methoxy-1,2,3,4-tetrahydronaphthalene

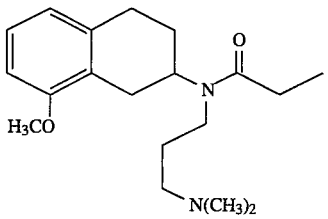

The solution of 1.30 g (5.0 mmol) of 2-(3-dimethylaminopropyl)amino-8-methoxy-1,2,3,4-tetrahydronaphthalene, 2.90 g (50 mmol) of propionaldehyde and 1.50 g (25 mmol) of glacial acetic acid was stirred for 30 minutes at 0° C. After addition of 0.70 g (10 mmol) of sodium cyanoborohydride, the mixture was stirred for 15 hours at room temperature. The reaction mixture was substantially concentrated in a rotary evaporator, taken up in tert.-butyl methyl ether, and stirred vigorously for 30 minutes with 20% strength sodium hydroxide solution. The aqueous phase was extracted carefully with tert.-butyl methyl ether. Washing the combined organic phases with water and saturated sodium chloride solution, drying over potassium carbonate, and concentrating in a rotary evaporator yielded the desired compound as a clear oil.

Yield: 1.50 g (98%) $R_f$ (chloroform/methanol/triethylamine 20:10:0.1): 0.26 IR (chloroform): 3040, 3007, 2936, 1653, 1587 MS: 304, 259, 232, 218, 204.

Example 18

2-[N-(3-Dimethylaminopropyl)-N-propyl]amino-8-methoxy-1,2,3,4-tetrahydronaphthalene dihydrochloride Using ethereal hydrochloric acid, 1.3 g (70%) of dihydrochloride were obtained from the compound of Example 17 as an amorphous, very hygroscopic powder.

Analysis ($C_{19}H_{32}N_2O_2 \times 2\ HCl \times H_2O$): Calc.: C 55.2 H 9.3 N 6.8 Cl 17.2 Found: C 55.8 H 9.1 N 6.3 Cl 17.3

Example 19

2-[N-(2-Diethylaminoethyl)-N-propyl]amino-8-methoxy-1,2,3,4-tetrahydronaphthalene

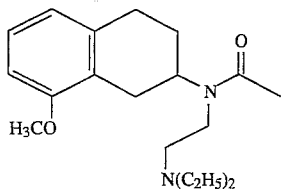

The solution of 1.20 g (4.3 mmol) of 2-(2-diethylaminoethyl)amino-8-methoxy-1,2,3,4-tetrahydronaphthalene, 2.50 g (43 mmol) of propionaldehyde and 0.80 g (13 mmol) of glacial acetic acid was stirred for 30 minutes at 0° C. 1.10 g (17 mmol) of sodium cyanoborohydride were subsequently added to the reaction mixture, which was stirred overnight at room temperature.

The reaction mixture was substantially concentrated in a rotary evaporator, taken up in tert.-butyl methyl ether, and stirred vigorously for 30 minutes with 20% strength sodium hydroxide solution. The aqueous phase was extracted carefully with tert.-butyl methyl ether. Washing the combined organic phases with water and saturated sodium chloride solution, drying over potassium carbonate and concentrating in a rotary evaporator yielded the crude product as an oil.

Chromatography on silica gel (toluene/ethyl acetate gradients) yielded 0.85 g (62%) of the title compound as a yellow oil.

$R_f$ (toluene/methanol 4:1): 0.17 MS: 318, 232, 161 IR (chloroform): 3058, 2972, 1586.

Example 20

2-[N-(2-Diethylaminoethyl)-N-propyl]amino-8-methoxy-1,2,3,4-tetrahydronaphthalene dihydrochloride The dihydrochloride, produced from the compound of Example 19 by treatment with ethereal hydrochloric acid, precipitated as an amorphous substance and was very hygroscopic.

Analysis ($C_{20}H_{34}N_2O \times 2$ HCl$\times 2$ $H_2O$): Calc.: C 56.2 H 9.4 N 6.6 Found: C 56.7 H 9.4 N 6.5

Example 21

2-[N-(2-Ethoxycarbonylamido-ethyl)-N-propyl]amino-8-methoxy-1,2,3,4-tetrahydronaphthalene

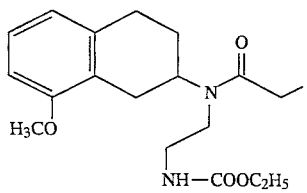

5.09 g (20 mmol) of 2-(2-ethoxycarbonylamidothyl)amino-8-methoxy-1,2,3,4-tetrahydronaphthalene, 11.6 g (200 mmol) of propionaldehyde and 2.40 g (40 mmol) of glacial acetic acid were stirred for 30 minutes at 0° C. in 150 ml of methanol. 2.50 g (40 mmol) of sodium cyanoborohydride were then added, and the mixture was stirred for 15 hours at room temperature.

The reaction mixture was substantially concentrated in a rotary evaporator, taken up in tert.-butyl methyl ether, and stirred vigorously for 30 minutes with sodium hydroxide solution/water at pH 10. The aqueous phase was extracted carefully with tert.-butyl methyl ether. Washing the combined organic phases with water and saturated sodium chloride solution, drying over magnesium sulphate, and concentrating in a rotary evaporator yielded the crude product as an oil. The crude product obtained was chromatographed on silica gel (toluene/ethanol gradients). 5.20 g (78%) of the desired compound were thus obtained as a pale brown oil.

$R_f$ (toluene/methanol 4:1): 0.25 IR (chloroform, $CHCl_3$): 3403, 2931, 1702, 1585.

Example 22

2-(2-Ethoxycarbonylamido-ethyl)-N-propyl]amino-8-methoxy-1,2,3,4-tetrahydronaphthalene hydrochloride The hydrochloride was produced as a foam from the compound of Example 21 using ethereal hydrochloric acid.

MS (C.I., reagent gas: $NH_3$): 335, 289, 232, 161

Example 23

2-(N-Quinuclidin-3-yl-N-propyl)amino-8-methoxy-1,2,3,4-tetrahydronaphthalene

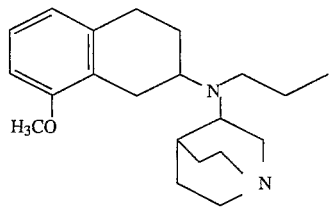

1.60 g (5.6 mmol) of 2-(quinuclidin-3-yl)amino-8-methoxy-1,2,3,4-tetrahydronaphthalene (obtained from 8-methoxy-2-tetralone and 3-aminoquinuclidine by reductive amination in the conventional fashion), 3.20 g (56 mmol) of propionaldehyde and 1.70 g (28 mmol) of glacial acetic acid were stirred for 30 minutes at 0° C. 0.80 g (11 mmol) of sodium cyanoborohydride was then added, and the mixture was stirred for 15 hours at room temperature. The reaction mixture was concentrated, taken up in toluene and reconcentrated, taken up in tert.-butyl methyl ether, and stirred vigorously for 30 minutes with 20% strength sodium hydroxide solution. The aqueous phase was extracted carefully with tert.-butyl methyl ether. Washing the combined organic phases with water and saturated sodium chloride solution, drying over potassium carbonate, and concentrating in a rotary evaporator yielded the crude product as an oil (2.0 g). Chromatography on silica gel (toluene/ethanol 3:1) supplied the title compound as a syrup.

Yield: 0.50 g (27%). $R_f$ (chloroform/methanol 2:1): 0.13 MS: 328, 216, 168, 160

Example 24

2-(N-Quinuclidin-3-yl-N-propyl)amino-8-methoxy-1,2,3,4-tetrahydronaphthalene dihydrochloride The dihydrochloride was precipitated in the form of colorless crystals from the ethereal solution of the compound of Example 23 using ethereal hydrochloric acid.

Melting point: 200°–205° C.

Example 25

2-(N-Cyanomethyl-N-propyl)amino-8-methoxy-1,2,3,4-tetrahydronaphthalene

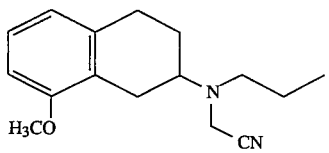

3.2 g (15 mmol) of 8-methoxy-2-propylamino-1,2,3,4-tetrahydronaphthalene, 5.6 g (72 mmol) of chloroacetonitrile and 9.6 g (72 mmol) of potassium carbonate were suspended in 65 ml of 2-butanone, 80 mg of sodium iodide were added, and the mixture was stirred overnight at 60° C. After filtration through Celite, the mixture was freed of solvent (rotary evaporator). After chromatography on silica gel (toluene/ethyl acetate gradients), 3.65 g (98%) of a pale yellow oil were obtained.

$R_f$ (toluene/methanol 4:1): 0.81 MS: 258, 229, 161

Example 26

2-(N-Cyanomethyl-N-propyl)amino-8-methoxy-1,2,3,4-tetrahydronaphthalene hydrochloride The hydrochloride was obtained, as colorless crystals, from the free base (Example 25) using ethereal hydrochloric acid.

Melting point: 164°–166° C.

Example 27

8-Methoxy-2-[N-propyl-N-(3-phthalimidoyl-propyl)]amino-1,2,3,4-tetrahydronaphthalene

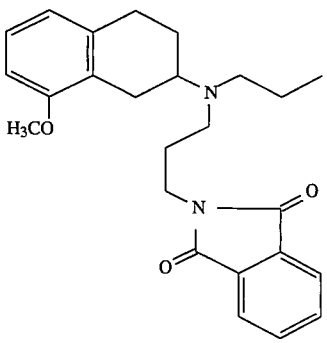

1.55 g (7.0 mmol) of 8-methoxy-2-N-propylamino-1,2,3,4-tetrahydronaphthalene, 1.40 g (14 mmol) of triethylamine, 1.90 g (7.0 mmol) of N-(S-bromopropyl)phthalimide and a spatula tip of sodium iodide were stirred for 4 hours at 60° C. in 35 ml of absolute dimethylformamide. After stripping off the solvent in a rotary evaporator (finally at 0.2 torr), the main product was obtained, as a yellowish oil, by flash chromatography on silica gel (toluene/ethyl acetate gradients, 0–33% ethyl acetate).

Yield: 0.90 g $R_f$ (toluene/ethyl acetate 1:1): 0.12

Example 28

8-Methoxy-2-[N-propyl-N-(3-phthalimidoyl-propyl)]amino-1,2,3,4-tetrahydronaphthalene hydrochloride The hydrochloride was obtained, as a colorless, hygroscopic solid, from Example 27 using ethereal hydrochloric acid.

Yield: 0.58 g Melting point: 80°–100° C.

Example 29

2-[N-(N,N-Diethylcarbamoylmethyl)-N-propyl]amino-8-methoxy-1,2,3,4-tetrahydronaphthalene

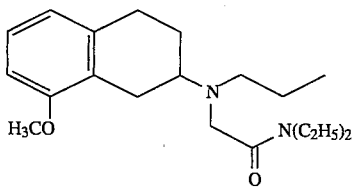

0.80 g (3.7 mmol) of 8-methoxy-2-propylamino-1,2,3,4-tetrahydronaphthalene, 2.75 g (18 mmol) of chloroacetic diethylamide, 2.50 g (18 mmol) of powdered potassium carbonate and 30 mg of sodium iodide in 10 ml of 2-butanone were reacted at 60° C. The reaction mixture was diluted with 100 ml of tert,-butyl methyl ether. Undissolved material was filtered off, and the solvent was removed. The residue remaining here was taken up in tert.butyl methyl ether. After acidification, the organic phase was separated off and discarded. The aqueous phase was basified and extracted with the last-mentioned solvent. After drying and concentrating the organic phase, 1.2 g of crude product remained as a brown oil.

$R_f$ (toluene/methanol 4:1): 0.5 MS (C.I. spectrum, reagent gas $NH_3$): 333 (M+1), 232, 161

Example 30

2-[N-(N,N-Diethylcarbamoylethyl)-N-propyl]amino-8-methoxy-1,2,3,4-tetrahydronaphthalene hydrochloride 795 mg (58%) of hydrochloride were obtained as a a pale brown solid from the crude product of Example 29 using ethereal hydrochloric acid.

MS (C.I., reagent gas: $NH_3$): 333 (M+1), 252, 161.

Example 31

2-(N-Ethoxycarbonylmethyl-N-propyl)amino-8-methoxy-1,2,3,4-tetrahydronaphthalene

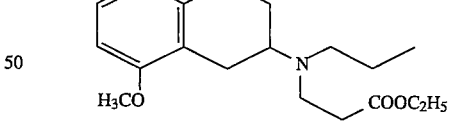

2.6 g (12 mmol) of 8-methoxy-2-propylamino-1,2,3,4-tetrahydronaphthalene, 1.7 g (12 mmol) of potassium carbonate, 6.0 g of molecular sieve (3A), 2.0 g (12 mmol) of ethyl bromoacetate and 100 mg of sodium iodide in 42 ml of ethanol were refluxed for 2 hours. After this time, a further 0.25 equivalents of potassium carbonate and 0.25 equivalents of ethyl bromoacetate were added, and the mixture was refluxed for a further 2 hours. Filtration through Celite and concentration supplied a crude product, which was purified by chromatography on silica gel (toluene/ethyl acetate gradients). In this fashion, 3.5 g of a colourless syrup (according to NMR, still contained about 4% of toluene) were obtained.

$R_f$ (toluene/methanol 4:1): 0.79 IR (chloroform): 1736, 1587, 1378, 1255.

Example 32

2-(N-Ethoxycarbonylmethyl-N-propyl)amino-8-methoxy-1,2,3,4-tetrahydronaphthalene hydrochloride 580 mg of hydrochloride were obtained as a colorless, amorphous, hygroscopic solid of 600 mg of the free base from Example 31 by treatment with ethereal hydrochloric acid.

Analysis ($C_{18}H_{27}NO_3 \times HCl \times H_2O$): Calc.: C 60.0 H 8.3 N 3.9 Found: C 60.0 H 8.4 N 3.7

Example 33

2-{4-[N-(8-Methoxy-1,2,3,4-tetrahydro-2-naphthyl)-N-propylamino]butyl}-1,2-benzisothiazol- 3(2H)-one 1,1-dioxide

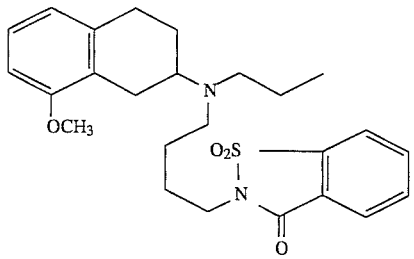

1.9 g (6.0 mmol) of 2-(4-bromobutyl)-1,2-benzisothiazol-3(2H)-one 1,1-dioxide were added dropwise to the solution of 1.3 g (6.0 mmol) of 8-methoxy-2-propylamino-1,2,3,4-tetrahydronaphthalene and 1.3 g (12 mmol) of triethylamine in 15 ml of dimethylformamide. After stirring for 15 hours at room temperature, a spatula tip of sodium iodide was added, and the mixture was heated to 60° C. After 4 hours at this temperature, 0.4 g of the above aminotetralin and 0.3 g of triethylamine were added. Chromatography on silica gel (toluene/ethyl acetate gradients) of the crude product, obtained after removal of the solvent in vacuo, yielded 0.70 g (25%) of the title compound as a yellowish oil.

$R_f$ (toluene/ethyl acetate 1:1): 0.36 MS: 456, 427, 232, 219, 196, 190, 161

Example 34

2-{4-[N-(8-Methoxy-1,2,3,4-tetrahydro-2-naphthyl)-N-propyl-amino]butyl}-1,2-benzisothiazol-3(2H)-one 1,1-dioxide hydrochloride The hydrochloride was obtained as a colorless solid by treatment of the compound of Example 33 with ethereal hydrochloric acid.

Melting range: 65°–80° C.

Example 35

2-[N-(3-Aminopropyl)-N-propyl]amino-8-methoxy-1,2,3,4-tetrahydronaphthalene

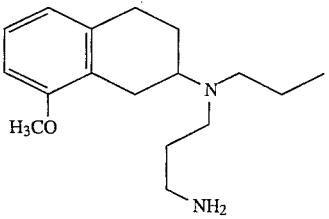

A solution of 12.2 g (45 mmol) of 2-[N-(2-cyanoethyl)-N-propyl]amino- 8-methoxy-1,2,3,4-tetrahydronaphthalene in 20 ml of ether was added carefully to 135 mmol of aluminum hydride in 100 ml of ether (prepared at 0° C. from 5.1 g of lithium aluminum hydride and a mixture of 3.3 g of 95% strength sulphuric acid and 3.3 g of 20% strength oleum in ether, with subsequent stirring for 1 hour at room temperature) at room temperature. The mixture was refluxed for 2 hours, and subsequently stirred for 15 hours at room temperature. After addition of 30 ml of water and 60 ml of 10% strength sodium hydroxide solution, the organic phase was separated off from the voluminous precipitate. The latter was leached three times with boiling ether. Drying the organic phase (potassium carbonate) and evaporation of the solvent yielded 9.30 g (75%) of a brown, viscous oil.

$R_f$ (chloroform/methanol/ammonia 30:10:1): 0.52 MS: 276, 247, 232

Example 36

2-[N-(2-Aminoethyl)-N-propyl]amino-8-methoxy-1,2,3,4-tetrahydronaphthalene

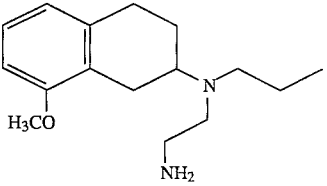

A mixture of 0.9 g of 95% strength sulphuric acid and 0.9 g of 20% strength oleum was added slowly to 1.4 g (13 mmol) of lithium aluminum hydride in 25 ml of ether at 0° C. After stirring for 1 hour at room temperature, a solution of 3.1 g (12 mmol) of 2-(N-cyanomethyl-N-propyl)amino-8-methoxy- 1,2,3,4-tetrahydronaphthalene in 5 ml of ether was added dropwise. The mixture was refluxed for 2 hours. 10 ml of water were then added carefully, followed by 20 ml of 10% strength sodium hydroxide solution. The undissolved material was separated off; this solid was washed several times with ether. After drying the organic phase over sodium carbonate and after removal of the solvent in vacuo (finally high vacuum), 2.3 g (73%) of the title compound were obtained as an oil.

$R_f$ (chloroform/methanol 2:1+1% triethylamine): 0.1 MS (C.I., reagent gas: $NH_3$): 263, 232, 161

Example 37

2-[N-(2-aminoethyl)-N-propyl]amino-8-methoxy-1,2,3,4-tetrahydronaphthalene dihydrochloride 1.3 g of dihydrochloride were obtained as a colorless solid by treatment of 1.0 g of the free base from Example 36 with ethereal hydrochloric acid.

Melting point: from 73° C., vitrification

Example 38

8-Methoxy-2-[N-(2-methylaminoethyl)-N-propyl]amino-1,2,3,4-tetrahydronaphthalene

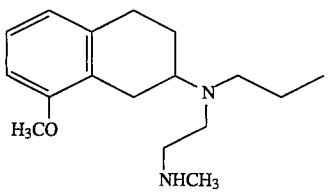

3.40 g (10 mmol) of 2-[N-(2-ethoxycarbonylamidoethyl)-N-propyl]-amino-8-methoxy- 1,2,3,4-tetrahydronaphthalene in 25 ml of ether were slowly added dropwise to the suspension of 0.75 g (20 mmol) of lithium aluminum hydride in 25 ml of ether at room temperature. After stirring overnight, the mixture was diluted with 15 ml of ether. 1 ml of water, 0.75 ml of sodium hydroxide solution and 3.0 ml of water were subsequently carefully added successively. For drying, 10 g of potassium carbonate were added, and the mixture was stirred for 20 minutes. Filtration and concentration supplied 2.7 g of crude product. Chromatography on silica gel (chloroform/methanol gradients), twice, yielded 0.60 g (33%) of the title compound as a colorless syrup.

$R_f$ (chloroform/methanol/triethylamine 2:1:0.01): 0.29

Example 39

8-Methoxy-2-[N-(2-methylaminoethyl)-N-propyl]amino-1,2,3,4-tetrahydronaphthalene dihydrochloride The dihydrochloride, produced as a very hygroscopic, amorphous, colorless solid, was obtained from the compound of Example 38 by treatment with ethereal hydrochloric acid.

Analysis ($C_{17}H_{28}N_2O \times 2$ HCl$\times H_2O$): Calc. C 55.6 H 8.8 N 7.6 Found C 55.4 H 8.7 N 7.3

Example 40

8-Methoxy-2-(1-methylpiperidin-4-yl)amino-1,2,3,4-tetrahydronaphthalene

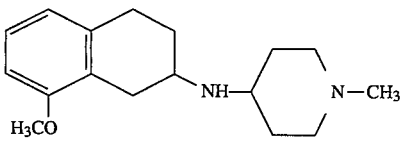

A solution of 1.20 g (3.6 mmol) of 2-(1-ethoxycarbonylpiperidin- 4-yl)amino-8-methoxy-1,2,3,4-tetrahydronaphthalene in 10 ml of ether was added dropwise at room temperature to the suspension of 0.27 g (7.2 mmol) of lithium aluminum hydride in 10 ml of ether. After stirring for 15 hours at room temperature, the mixture was diluted with 30 ml of ether. 0.3 ml of water, 0.25 ml of 20% strength sodium hydroxide solution and 1 ml of water were subsequently carefully added dropwise. For drying, 3 g of potassium carbonate were added, and the mixture was stirred for 20 minutes. By filtration and concentration (finally high vacuum), 0.90 g (91%) of the title compound was obtained as an oil.

$R_f$ (chloroform/methanol/triethylamine 20:10:0.1): 0.26

Example 41

8-Methoxy-2-(1-methylpiperidin-4-yl)amino-1,2,3,4-tetrahydronaphthalene dihydrochloride The dihydrochloride, obtained by reaction of the compound from Example 40 with ethereal hydrochloric acid, precipitated in the form of pale yellow crystals.

Melting point: >260° C. Analysis ($C_{17}H_{26}N_2O \times 2$ HCl$\times H_2O$) Calc.: C 56.2 H 8.3 N 7.7 Found: C 55.9 H 8.2 N 7.7

Example 42

2-[N-(2-Hydroxyethyl)-N-propyl]amino-8-methoxy-1,2,3,4-tetrahydronaphthalene

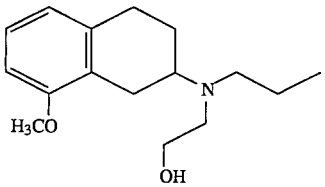

2.9 g (9.5 mmol) of 2-(N-ethoxycarbonylethyl-N-propyl)amino-8-methoxy-1,2,3,4-tetrahydronaphthalene in 20 ml of ether were added dropwise to the suspension of 0.22 g (5.7 mmol) of lithium aluminium hydride in 10 ml of ether. After stirring for 1 hour at room temperature, 0.3 ml of water, 0.35 ml of 20% strength sodium hydroxide solution and 1.0 ml of water were added successively. Drying agent (magnesium sulphate) was added, and the mixture was stirred for 20 minutes at room temperature, filtered through Celite, and freed of solvent in vacuo (finally in a high vacuum). 1.8 g (72%) of a clear oil remained.

$R_f$ (toluene/ethanol 6:1): 0.25 MS: 263, 232, 161 IR (chloroform): 3670, 3430, 1587.

Example 43

2-[N-(2-Carbamoylethyl)-N-propyl]amino-8-methoxy-1,2,3,4-tetrahydronaphthalene

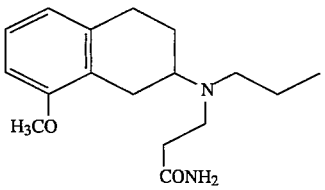

0.54 g (2.0 mmol) of 2-[N-(2-cyanoethyl)-N-propyl]amino-8-methoxy-1,2,3,4-tetrahydronaphthalene were stirred for 2 hours at room temperature with 2 ml of concentrated hydrochloric acid. After dilution with 20 ml of water, the mixture was adjusted to pH 7 using 20% strength sodium hydroxide solution, with cooling, and the aqueous phase was extracted carefully with ethyl acetate. The crude product, obtained after drying and concentrating the organic phase, was purified by chromatography on aluminum oxide (neutral, activity III) using toluene/ethyl acetate gradients.

$R_f$ (aluminum oxide, toluene/ethyl acetate 1:1): 0.1 MS: 290, 261, 232, 161

Example 44

2-[N-(2-Carbamoylethyl)-N-propyl]amino-8-methoxy-1,2,3,4-tetrahydronaphthalene hydrochloride The hydrochloride was obtained, as a colorless solid, from the compound of Example 43 by treatment with ethereal hydrochloric acid in ether.

Melting point: 80° C. (vitrification from 65° C.)

Example 45

8-Methoxy-2-{N-[2-(4-toluene-sulphonamido)ethyl]-N-propyl}amino-1,2,3,4-tetrahydronaphthalene hydrochloride

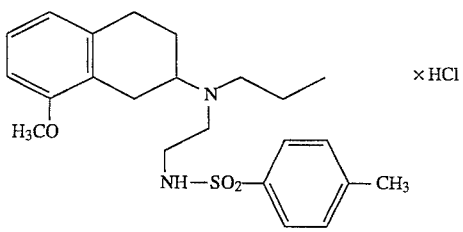

0.77 g (4.0 mmol) of tosyl chloride in 5 ml of dichloromethane was added dropwise to the solution of 1.00 g (4.0 mmol) of 2-[N-(2-aminoethyl)-N-propyl]amino-8-methoxy-1,2,3,4-tetrahydronaphthalene in 10 ml of dichloromethane at 0° C. After stirring for 15 hours at room temperature, the mixture was freed of solvent in vacuo. Digestion of the residue in ether yielded 1.6 g of the hydrochloride of the title compound as a yellowish, microcrystalline solid.

Melting range: from 100° C., with decomposition

Example 46

8-Methoxy-2-{N-[2-(4-toluene-sulphonamido)ethyl]-N-propyl}amino-1,2,3,4-tetrahydronaphthalene The free base is obtained by treatment of the compound from Example 45 with sodium bicarbonate solution.

$R_f$ (toluene/ethanol 3:1): 0.53

Example 47

2-{N-[3-(4-Fluorophenylsulphonamido)propyl]-N-propyl}amino-8-methoxy-1,2,3,4-tetrahydronaphthalene hydrochloride

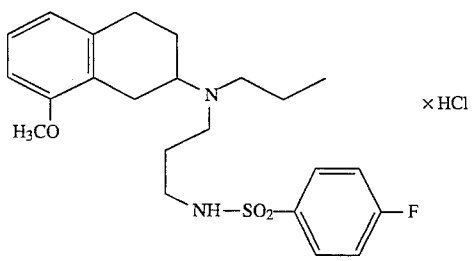

0.39 g (2.0 mmol) of 4-fluorophenylsulphonyl chloride in 5 ml of methylene chloride was added dropwise to the solution of 0.55 g (2.0 mmol) of 2-[N-(3-aminopropyl)-N-propyl]amino-8-methoxy- 1,2,3,4-tetrahydronaphthalene in 8 ml of methylene chloride at 0° C. After stirring for 15 hours at room temperature, the mixture was concentrated and the hydrochloride was precipitated, in the form of beige crystals, from ethanolic solution by addition of ether.

Yield: 0.82 g (94%) Melting range: 120°–140° C. (after vitrification) MS: 434, 405, 232, 219, 186, 161

Example 48

2-{N-[3-(4-Fluorophenylsulphonamido)propyl]-N-propyl}amino-8-methoxy-1,2,3,4-tetrahydronaphthalene The free base was obtained by treatment of the compound of Example 47 with sodium bicarbonate solution.

$R_f$ (toluene/ethanol 3:1): 0.45

Example 49

2-[N-(2-Methanesulphonamidoethyl)-N-propyl]amino-8-methoxy-1,2,3,4-tetrahydronaphthalene hydrochloride

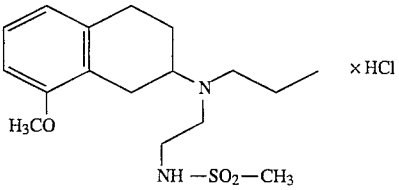

230 mg (2.0 mmol) of methanesulphonyl chloride in 2 ml of methylene chloride were added dropwise to the solution of 520 mg (2.0 mmol) of 2-[N-(2-aminoethyl)-N-propyl]amino-8-methoxy- 1,2,3,4-tetrahydronaphthalene in 5 ml of methylene chloride at 0° C. After stirring for 15 hours at room temperature, the mixture was freed of solvent in a rotary evaporator at a maximum bath temperature of +25° C. Digestion of the residue with diethyl ether yielded 673 mg (89%) of hydrochloride after drying the solid in a high vacuum.

Melting point: from 100° C., with decomposition. MS (C.I., reagent gas: $NH_3$): 341 (M+1), 232, 161

Example 50

2-N-(2-Methanesulphonamidoethyl)-N-propyl]-8-methoxy-1,2,3,4-tetrahydronaphthalene The free base was obtained by treatment of the compound of Example 49 with sodium bicarbonate solution.

$R_f$ (chloroform/methanol 2:1): 0.65

Example 51

2-{N-[2-(3-Chloropropylsulphonamido)ethyl]-N-propyl}amino-8-methoxy-1,2,3,4-tetrahydronaphthalene

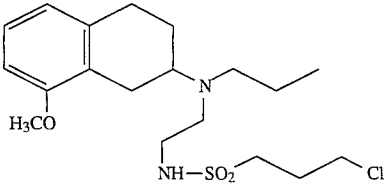

1.80 g (10 mmol) of 3-chloropropanesulphonyl chloride in 20 ml of dichloromethane were slowly added dropwise, at 0° C. to the solution of 2.70 g (10 mmol) of 2-[N-(2-aminoethyl)-N-propyl]amino- 8-methoxy-1,2,3,4-tetrahydronaphthalene 50 ml of dichloromethane, excluding moisture. After 15 hours at room temperature, the mixture was diluted with 150 ml of ethyl acetate and 50 ml of water. The pH was adjusted to 7 using sodium hydroxide solution. Extraction with ethyl acetate, washing of the organic phase with saturated sodium chloride solution, and drying over magnesium sulphate yielded 4.3 g of crude product, after evaporation of the solvent.

Flash chromatography on silica gel (toluene/ethyl acetate gradients) supplied 4.10 g of pure product, still slightly contaminated by solvent.

$R_f$ (toluene/ethanol 3:1): 0.62 IR (chloroform): 3319, 3019, 2961, 1587, 1470 MS (C.I., reagent gas: $NH_3$): 405/403 (M+1), 367, 232, 161.

Example 52

2-{N-[2-(3-Chloropropylsulphonamido)ethyl]-N-propyl}amino-8-methoxy-1,2,3,4-tetrahydronaphthalene hydrochloride The hydrochloride was obtained, in a yield of 92%, as a pale yellowish, hygroscopic solid, from the free base of Example 51 using ethereal hydrochloric acid.

Melting range: 60°–70° C.

Example 53

2-{N-[2-(4-Chlorobutanesulphonamido)ethyl]-N-propyl}amino-8-methoxy-1,2,3,4-tetrahydronaphthalene

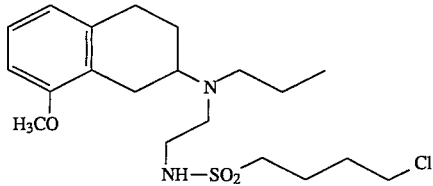

2.00 g (10 mmol) of 4-chlorobutanesulphonyl chloride in 20 ml of dichloromethane were slowly added dropwise to the solution of 2.70 g (10 mmol) of 2-[N-(2-aminoethyl)-N-propyl]amino- 8-methoxy-1,2,3,4-tetrahydronaphthalene in 50 ml of dichloromethane at 0° C., excluding moisture. After 15 hours at room temperature, the mixture was diluted with 150 ml of ethyl acetate and 50 ml of water. The pH of the mixture was adjusted to 7 using sodium hydroxide solution. Extraction with ethyl acetate, washing of the organic phase with saturated sodium chloride solution and drying over magnesium sulphate yielded 4.5 g of crude product, after evaporation of the solvent.

Flash chromatography on silica gel (toluene/ethyl acetate gradients) gave 3.2 g (77%) of the title compound as a syrup.

$R_f$ (toluene/ethanol/triethylamine 30:10:0.5): 0.46 IR (chloroform): 3296, 3010, 2964, 1587, 1470 MS (C.I., reagent gas: $NH_3$): 419/417 (M+1), 381, 232, 161.

Example 54

2-{N-[2-(4-Chlorobutanesulphonamido)ethyl]-N-propyl}amino-8-methoxy-1,2,3,4-tetrahydronaphthalene hydrochloride The hydrochloride was obtained, as a pale yellowish, hygroscopic solid, from the free base (compound 53) using ethereal hydrochloric acid.

Melting point: 70° C.

Example 55

2-{2-[N-propyl-N-(8-methoxy-1,2,3,4-tetrahydro-2-naphthyl)]amino}ethyl-isothiazolidine 1,1-dioxide

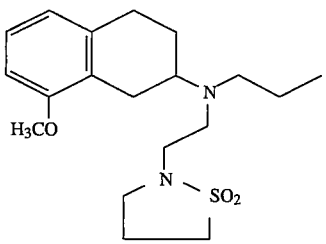

1.60 g (4.0 mmol) of 2-{N-[2-(3-chloropropylsulphonamido)ethyl]-N-propyl}amino- 8-methoxy-1,2,3,4-tetrahydronaphthalene in 3 ml of dimethylformamide were added to the suspension of 144 mg (4.8 mmol) of sodium hydride (80% strength in paraffin) and a spatula tip of sodium iodide in 20 ml of dimethylformamide. After stirring for 1 hour at room temperature, 0.3 ml of water was added. After concentrating in a rotary evaporator, the mixture was distributed between toluene and water. 1.2 g (82%) of the title compound were obtained as an oil by thorough extraction, drying over magnesium sulphate and concentrating.

$R_f$ (toluene/ethyl acetate 1:1): 0.28 MS (C.I., reagent gas: $NH_3$): 367 (M+1), 232

Example 56

2-{2-[N-Propyl-N-(8-methoxy-1,2,3,4-tetrahydro-2-naphthyl)]amino}ethyl-isothiazolidine 1,1-dioxide hydrochloride The hydrochloride of the compound of Example 55 was obtained as a colorless, hygroscopic solid by treatment with ethereal hydrochloric acid in ether.

Melting point: 90°–100° C.

Example 57

2-[2-N-Propyl-N-(8-methoxy-1,2,3,4-tetrahydro-2-naphthyl)amino]ethyl-perhydro-1,2-thiazine 1,1-dioxide

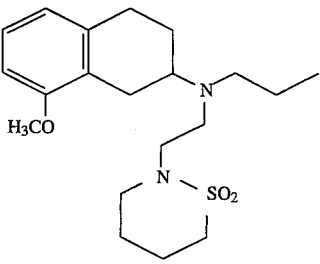

1.46 g (3.5 mmol) of 2-{N-[2-(4-chlorobutanesulphonamido)ethyl]-N-propyl}amino- 8-methoxy-1,2,3,4-tetrahydronaphthalene in 7 ml of dimethylformamide were added to the suspension of 126 mg (4.2 mmol) of sodium hydride (80% strength in paraffin) and 175 mg (1.1 mmol) of sodium iodide in 18 ml of dimethylformamide. After stirring for 1 hour at room temperature, 0.1 ml of water was added. After concentrating in a rotary evaporator, the mixture was distributed between toluene and water. 1.2 g (90%) of the title compound was obtained as an oil by thorough extraction, drying over magnesium sulphate and concentrating.

$R_f$ (toluene/ethyl acetate 1:1): 0.4 MS (C.I., reagent gas:

NH$_3$): 381 (M+1), 232, 161

Example 58

2-[2-N-Propyl-N-(8-methoxy-1,2,3,4-tetrahydro-2-naphthyl)amino]ethyl-perhydro- 1,2-thiazine 1,1-dioxide hydrochloride The hydrochloride was obtained, as a colorless, hygroscopic solid, by treatment of the compound of Example 57 with ethereal hydrochloric acid in ether.

Melting point: 80°–90° C.

Example 59

2-{N-[2-(N,N-Dimethylaminosulphonamido)]ethyl-N-propyl}amino-8-methoxy-1,2,3,4-tetrahydronaphthalene

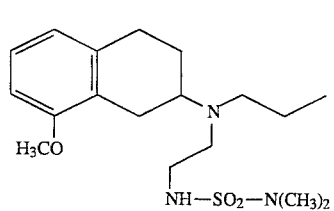

0.30 g (2.0 mmol) of dimethylamidosulphonyl chloride in 5 ml of anhydrous methylene chloride was slowly added dropwise at 0° C. to the solution of 0.53 g (2.0 mmol) of 2-[N-(2-aminoethyl)-N-propyl]amino-8-methoxy-1,2,3,4-tetrahydronaphthalene in 8 ml of anhydrous methylene chloride. After stirring overnight, the mixture was diluted with 50 ml of ethyl acetate and 30 ml of water, the pH was adjusted to 7 using sodium hydroxide solution, and the organic phase was separated off. Drying the organic phase (magnesium sulphate) and concentrating supplied 0.6 g of crude product.

Flash chromatography on silica gel (toluene/ethyl acetate gradients) yielded 0.38 g (52%) of the title compound as a colorless syrup.

R$_f$ (toluene/ethanol triethylamine 30:10:0.5): 0.47 IR (chloroform): 3009, 2929, 1584, 1468, 1372 MS (C.I., reagent gas: NH$_3$): 370 (M+1), 232, 153, 121.

Example 60

2-{N-[2-(N,N-Dimethylaminosulphonamido)]ethyl-N-propyl}amino-8-methoxy-1,2,3,4-tetrahydronaphthalene hydrochloride The hydrochloride of the compound 59 is obtained as a hygroscopic solid using ethereal hydrochloric acid.

Melting point: 65°–70° C.

Example 61

8-Methoxy-2-[N-propyl-N-(2-nicotinoylamido-propyl)]amino-1,2,3,4-tetrahydronaphthalene

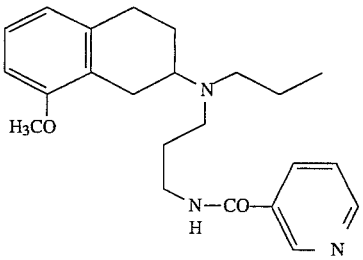

20 mg of sodium hydride suspension (80% strength in paraffin) were added to the solution of 0.55 g (2.0 mmol) of 2-(N-3-aminopropyl-N-propyl)amino-8-methoxy-1,2,3,4-tetrahydronaphthalene and 0.28 g (2.0 mmol) of methyl nicotinate in 20 ml of tetrahydrofuran, and the mixture was refluxed for 5 hours. The solvent was removed in a rotary evaporator. The remaining residue was taken up in 30 ml of toluene and 30 ml of ice-cold pH 7 buffer. Phase separation, extraction of the aqueous phase with ethyl acetate, drying the combined organic phases over magnesium sulphate, and evaporation of the solvent yielded 680 mg of crude product. This crude product was purified by flash chromatography on silica gel (eluent: toluene, toluene/ethyl acetate 1:1 and toluene/ethanol 5:1). 520 mg (76%) of the title compound were obtained as a brownish syrup.

R$_f$ (HPTLC prepared plate NH$_2$ F254s, Merck; toluene/ethyl acetate 1:1): 0.3

Example 62

8-Methoxy-2-[N-propyl-N-(2-nicotinoylamido-propyl)]amino-1,2,3,4-tetrahydronaphthalene dihydrochloride The dihydrochloride was obtained, as a colorless, hygroscopic solid, from the compound of Example 61 using ethereal hydrochloric acid.

Melting point: 110° C. Example 63
N-6-Chlorohexyl-N'-{3-[N-(8-methoxy-1,2,3,4-tetrahydro-2-naphthyl)-N-propyl]aminopropyl}-urea

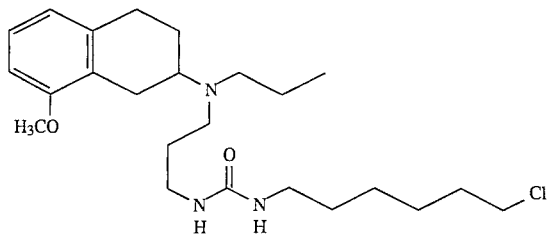

330 mg (2.0 mmol) of 6-chlorohexyl isocyanate in 3 ml of tetrahydrofuran were slowly added dropwise, at 0° C., to the solution of 550 mg (2.0 mmol) of 2-[N-(3-aminopropyl)-N-propyl]amino- 8-methoxy-1,2,3,4-tetrahydronaphthalene in 10 ml of anhydrous tetrahydrofuran. After 1 hour at 0° C., the mixture was stirred for a further 1 hour at room temperature. The crude product, obtained after evaporation of the solvent, was purified by flash chromatography on silica gel (toluene/methanol gradients).

Yield: 950 mg of a yellowish syrup (still contained residual solvent) $R_f$ (toluene/methanol 4:1): 0.26 MS: 439/437, 410/408, 396/394, 372, 232, 161

Example 64

N-6-Chlorohexyl-N'-{3-[N-(8-methoxy-1,2,3,4-tetrahydro-2-naphthyl)-N-propyl]aminopropyl}urea hydrochloride Treatment of the compound from Example 64 with ethereal hydrochloric acid supplied the hydrochloride as a colorless, amorphous solid (795 mg).

$^1$H NMR (CD$_3$OD): =1.05 (t, 2H); 1.25–2.05 (m, 13H); 2.30 (m, 1H); 2.78 (m, 1H); 2.9–3.6 (m); 3.75 (m, 1H); 3.85 (s, 3H); 6.7 (m, 2H); 7.15 (m, 1H).

Example 65

N-{2-[N-(8-Methoxy-1,2,3,4-tetrahydro-2-naphthyl)-N-propyl]aminoethyl}-N'-phenyl-urea

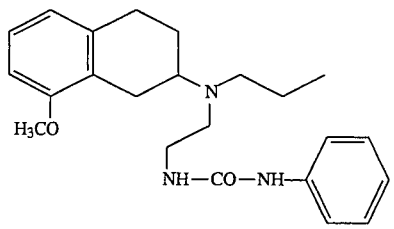

0.50 g (1.91 mmol) of 2-[N-(2-aminoethyl)-N-propyl]amino- 8-methoxy-1,2,3,4-tetrahydronaphthalene was dissolved in 10 ml of tetrahydrofuran, and 0.23 g (1.92 mmol) of phenyl isocyanate in the same amount of tetrahydrofuran were slowly added at 0° C. After 1 hour at 0° C. and 1 hour at room temperature, the mixture was concentrated. The crude product was purified by flash chromatography on silica gel (toluene/methanol gradients). 0.60 g (82%) of the title compound were thus obtained as a syrup.

$R_f$ (toluene/ethanol/triethylamine 3:1:0.05): 0.35 IR (chloroform): 3430, 3360, 3030, 1666 MS (FAB): 382 (M+1), 232, 161.

Example 66

N-{2-[N-(8-Methoxy-1,2,3,4-tetrahydro-2-naphthyl)-N-propyl]aminoethyl}-N'-phenyl-urea hydrochloride The hydrochloride was obtained, as an amorphous, hygroscopic solid, from the free base of Example 65 using ethereal hydrochloric acid.

Analysis (C$_{23}$H$_{31}$N$_3$O$_2$×HCl×H$_2$O): Calc.: C 63.5 H 7.8 N 9.6 Found: C 64.0 H 7.8 N 10.1

Example 67

2-[N-(2-Ethyl-carbonyldioxy-ethyl)-N-propyl]amino-8-methoxy-1,2,3,4-tetrahydronaphthalene

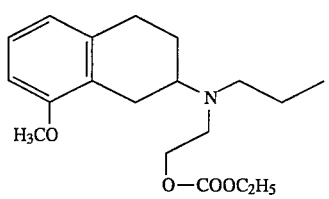

A solution of 0.50 g (4.4 mmol) of ethyl chloroformate in 15 ml of methylene chloride was added dropwise at 0° C. to the solution of 0.70 g (8.8 mmol) of pyridine and 1.10 g (4.0 mmol) of 2-[N-(2-hydroxyethyl)-N-propyl]amino- 8-methoxy-1,2,3,4-tetrahydronaphthalene in 20 ml of methylene chloride. After stirring for 15 hours at room temperature, the mixture was filtered, and the organic phase was washed with water and saturated sodium chloride solution. Drying (magnesium sulphate) and concentrating supplied 0.8 g of crude product. Chromatography on silica gel (toluene/ethyl acetate gradients) gave 0.25 g (19%) of the title compound.

$R_f$ (toluene/ethyl acetate 3:1): 0.56 MS: 335, 306, 232, 176, 161

Example 68

2-[N-(2-Ethyl-carbonyldioxy-ethyl)-N-propyl]amino-8-methoxy-1,2,3,4-tetrahydronaphthalene hydrochloride The hydrochloride of the compound from Example 67 can be obtained as a colorless, amorphous solid using ethereal hydrochloric acid.

$^1$H NMR (CD$_3$OD): =1.05 (t, 3H); 1.38 (t, 3H); 1.82 (m, 3H); 2.35 (m, 1H); 2.7–3.85 (m); 4.25 (q, 2H); 4.5 (m, 2H); 6.75 (m, 2H); 7.15 (m, 1H).

Example 69

2-[N-(2-Cyanoethyl)-N-propyl]amino-8-methoxy-1,2,3,4-tetrahydronaphthalene

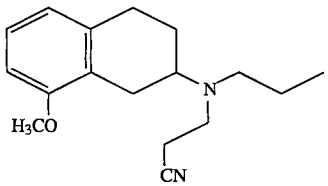

1.10 g (5.0 mmol) of 8-methoxy-2-propylamino-1,2,3,4-tetrahydronaphthalene, 1.30 g (25 mmol) of acrylonitrile and 20 mg of copper acetate were stirred for 3.5 hours at 100° C. Flash chromatography of the reaction batch on silica gel (toluene/ethyl acetate gradient) yielded 1.10 g (81%) of the title compound as a yellowish oil.

$R_f$ (toluene/ethyl acetate 3:1): 0.62 MS: 272, 243, 232, 161 IR (chloroform): 2249, 1587.

Example 70

2-[N-(2-Cyanoethyl)-N-propyl]amino-8-methoxy-1,2,3,4-tetrahydronaphthalene hydrochloride The hydrochloride was obtained, as a colorless solid, from the compound of Example 69 using ethereal hydrochloric acid.

Melting range: 60°–67° C.

The following was prepared analogously to Examples 1 to 12:

Example 71

2-[3-(Indol-3-yl)propyl]amino-8-methoxy-1,2,3,4-tetrahydronaphthalene

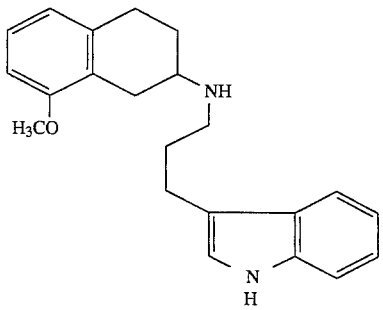

Melting point: 154° C.

The following were prepared analogously to Example 17 to 24:

Example 72

2-N-propyl-N-[3-(1,2,3,4-tetrahydronaphthalen-1-yloxy)propyl]amino- 8-methoxy-1,2,3,4-tetrahydronaphthalene hydrochloride (diastereomeric mixture)

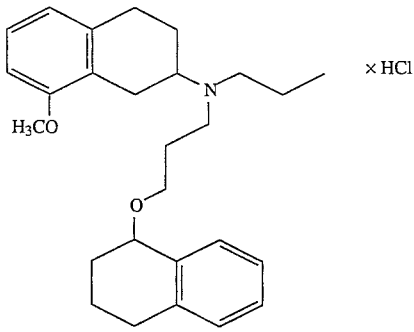

$^1$H NMR (CD$_3$OD): δ=1.0 (m, 3H); 1.6–2.3 (m, 10H); 2.6–3.9 (m,); 4.5 (m, 1H); 6.7 (2d, 2H); 7.0–7.4 (m, 5H).

Example 73

2-{N-[3-(Indol-3-yl)propyl]-N-propyl}amino-8-methoxy-1,2,3,4-tetrahydronaphthalene dihydrochloride

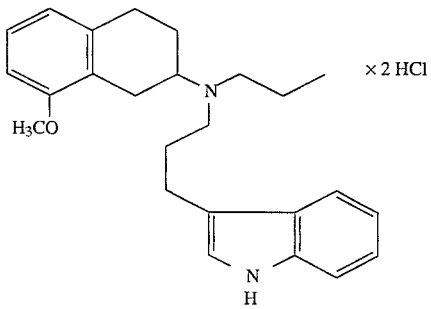

Melting range: 70°–130° C. (hygroscopic) $^1$H NMR (CD$_3$OD): δ=0.95 (t, 3H); 1.6–1.9 (m, 3H); 2.1–2.2 (m, 3H); 2.6–3.75 (m,); 3.8 (s, 3H); 6.7 (2d, 2H); 6.9–7.1 (m,); 7.35 (d, 1H); 7.55 (d, 1H).

Example 74

2-{N-[2-(Indol-3-yl)ethyl]-N-propyl}amino-8-methoxy-1,2,3,4-tetrahydronaphthalene dihydrochloride

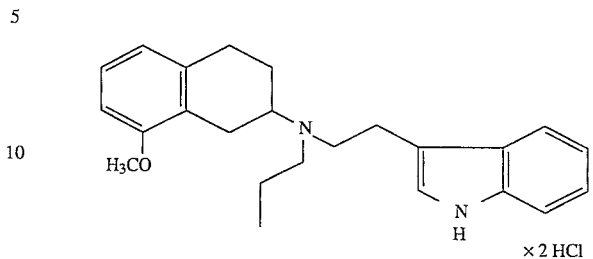

Melting point: >100° C. $^1$H NMR (CD$_3$OD): δ=1.05 (t, 3H); 1.7–2.0 (m, 3H); 2.3 (m, 1H); 2.7–3.9 (m,); 6.6–6.8 (m, 2H); 7.0 (m, 3H); 7.25 (d, 1H); 7.4 (d, 1H); 7.6 (dd, 1H).

Example 75

2-[N-(3-Phenylthio-propyl)-N-propyl)amino-1,2,3,4-tetrahydronaphthalene hydrochloride

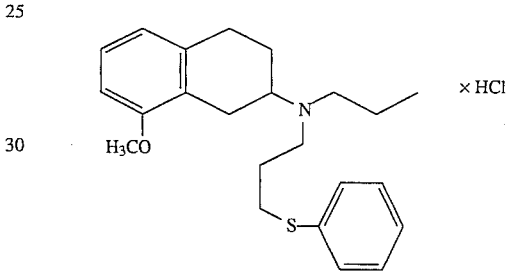

$^1$H NMR (CD$_3$OD): δ=1.0 (d, 3H); 1.6–1.9 (m, 3H); 2.1 (m, 2H); 2.25 (m, 1H); 2.1–3.5 (m,); 3.65 (m, 1H); 3.8 (s, 3H); 6.7 (d, 1H); 6.75 (d, 1H); 7.15 (dd, 1H); 7.15–7.4 (m, 5H),

The following were prepared analogously to Example 25 to 34:

Example 76

2-[N-4-(4,4-Dimethyl-2,6-dioxo-piperidin-1-yl)butyl-N-propyl]amino- 8-methoxy-1,2,3,4-tetrahydronaphthalene hydrochloride

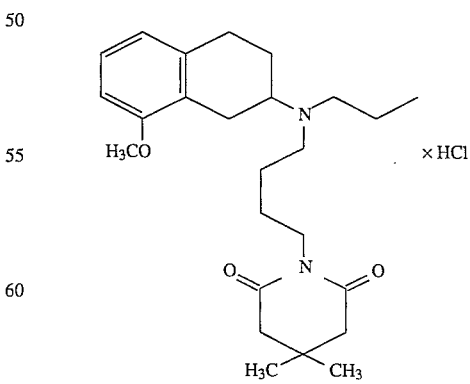

$^1$H NMR (CD$_3$OD): δ=1.0–1.1 (m, 9H); 1.6–2.0 (m, 7H) 2.3 (m, 1H); 2.55 (s, 4H); 2.8–3.9 (m,); 6.85 (2d, 2H), 7.1 (dd, 1H).

Example 77

2-{3-[N-(8-Methoxy-1,2,3,4-tetrahydronaphthalen-2-yl)-N-propyl-amino]propyl}- 1,2-benzisothiazol-3(2H)-one 1,1dioxide hydrochloride

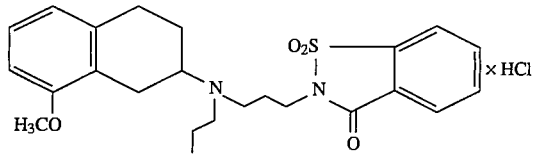

$^1$H NMR (CDCl$_3$): δ=1.0 (t, 3H); 1.8–2.2 (m); 2.5–4.0, (m); 6.6–6.8 (m, 2H); 7.15 (dd, 1H); 7.8–8.2 (m, 4H) 12.3 (1H).

Example 78

2-{4-[N-(8-Methoxy-1,2,3,4-tetrahydronaphthalen-2-yl)-N-propyl-amino]but- 2-enyl}-1,2-benzisothiazol-3(2H)-one 1,1-dioxide (trans-form)

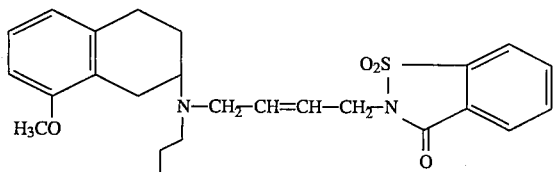

IR (chloroform): 3008, 2935, 2840, 1732, 1587, 1470, 1440.

Example 79

2-{4-[N-(8-Methoxy-1,2,3,4-tetrahydronaphthalen-2-yl)-N-propyl-amino]but- 2-enyl}-1,2-benzisothiazol-3(2H)-one 1,1-dioxide hydrochloride (trans form)

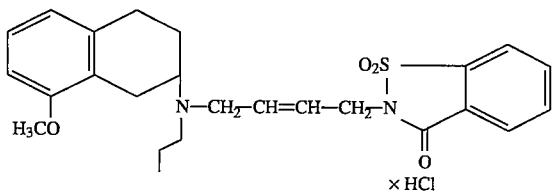

Example 80

2-{5-[N-(8-Methoxy-1,2,3,4-tetrahydronaphthalen-2-yl)-N-propyl-amino]pentyl}- 1,2-benzisothiazol-3(2H)-one 1,1-dioxide hydrochloride

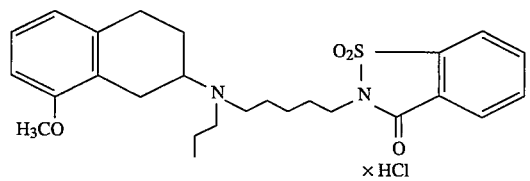

$^1$H NMR (CD$_3$OD): δ=1.05 (t, 3H); 1.5 (m, 2H); 1.7–2.0 (m, 7H); 2.3 (m, 1H); 2.7–3.9 (m); 6.7 (2d, 2H); 7.15 (t, 1H); 7.9–8.1 (m, 4H).

Example 81

2-{2-[N-(8-Methoxy-1,2,3,4-tetrahydronaphthalen-2-yl)-N-propyl-amino]propyl}- 1,2-benzisothiazol-3(2H)-one 1,1-dioxide hydrochloride

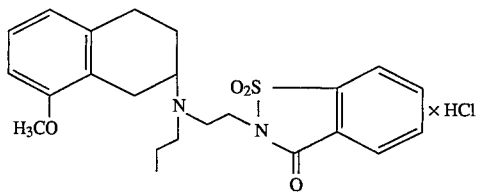

Melting range: 90°–110° C. (hygroscopic) $^1$H NMR (CD$_3$OD): δ=1.05 (t, 3H); 1.7–2.0 (m, 3H); 2.3 (m, 1H); 2.7–4.1 (m); 3.8 (s, 3H); 4.3 (m, 2H); 6.75 (2d, 2H); 7.15 (dd, 1H); 7.9–8.2 (m, 4H).

Example 82

2-[N-(2-Cyano-benzyl)-N-propyl]amino-8-methoxy-1,2,3, 4-tetrahydronaphthalene

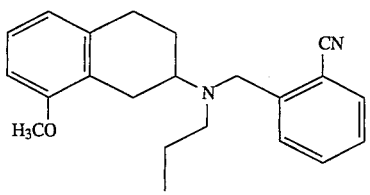

IR (chloroform): 3010, 2965, 2938, 2227, 1603, 1588, 1471, 1441.

Example 83

2-[N-(3-Cyano-benzyl)-N-propyl]amino-8-methoxy-1,2,3, 4-tetrahydronaphthalene

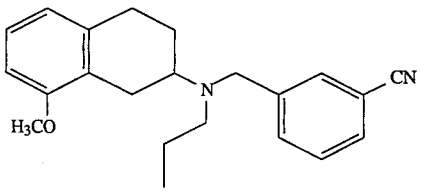

IR (chloroform): 3008, 2964, 2938, 2842, 2234, 1604, 1588, 1471, 1442.

Example 84

2-[N-(4-Cyano-benzyl)-N-propyl]amino-8-methoxy-1,2,3, 4-tetrahydronaphthalene

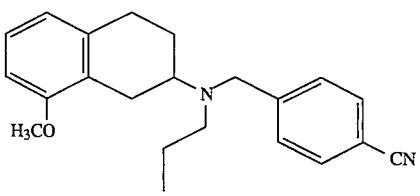

IR (chloroform): 3010, 2934, 2876, 2230, 1610, 1588, 1471, 1441.

The following were prepared analogously to Examples 45 to 54:

Example 85

2-{N-[3-(4-Methylphenylsulphonamido)propyl]-N-propyl}amino-8-methoxy-1,2,3,4-tetrahydronaphthalene hydrochloride

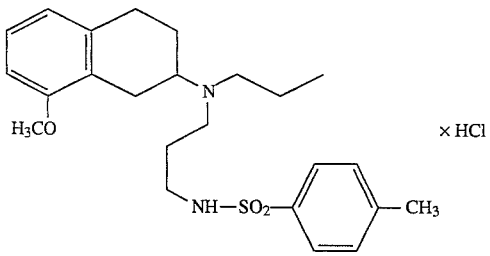

Melting range: 80°–90° C. $^1$H NMR (CD$_3$OD): δ=1.05 (t, 3H); 1.7–2.0 (m, 5H); 2.25 (m, 1H); 2.4 (s, 3H); 2.6–3.8 (m); 3.85 (s, 3H); 6.75 (2d, 2H); 7.15 (dd, 1H); 7.45 (d, 2H); 7.75 (d, 2H).

Example 86

2-{N-[3-(3-Ethoxycarbonyl-propylsulphonamido)propyl]-N-propyl}amino- 8-methoxy-1,2,3,4-tetrahydronaphthalene hydrochloride

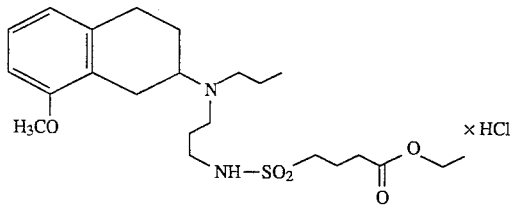

Melting point: >50° C. $^1$H NMR (CD$_3$OD): δ=1.0 (2t, 3H); 1.25 (t, 3H); 1.8–2.2 (m, 7H); 2.35 (m, 1H), 2.5 (m, 2H); 2.7–3.9 (m); 3.85 (s, 3H); 4.1 (q, 2H); 6.75 (2d, 2H); 7.15 (dd, 1H).

Example 87

2-{N-[2-[N',N'-Bis(4-methylphenylsulphonyl)amino]ethyl]-N-propyl}amino- 1,2,3,4-tetrahydronaphthalene hydrochloride

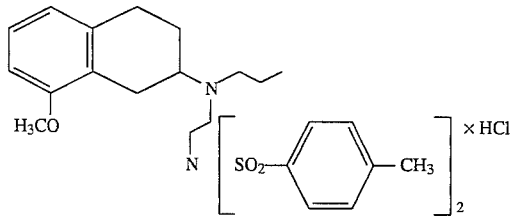

Melting range: 105°–110° C.

Example 88

2-[N-3-Benzyloxycarbonylamido)propyl-N-propyl]amino-8-methoxy-1,2,3,4-tetrahydronaphthalene hydrochloride

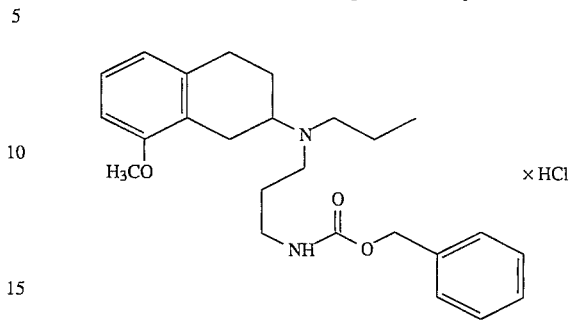

$^1$H NMR (CD$_3$OD): δ=1.05 (t, 3H); 1.7–2.1 (m, 5H); 2.25 (m, 1H), 2.6–3.8 (m); 3.85 (s, 3H); 5.1 (ws, 2H); 6.75 (2d, 2H); 7.15 (t, 1H); 7.2–7.4 (m, 5H).

Example 89

2-{4-[N-(8-Methoxy-1,2,3,4-tetrahydro-2-naphthyl)-N-propyl-amino]but- 2-inyl}-1,2-benzisothiazol-3(2H)-one 1,1-dioxide

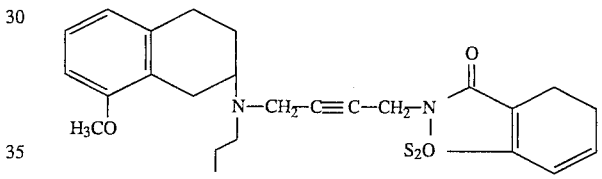

2.21 g of propargylsaccharine in 20 ml of dioxane added dropwise to 2.19 g (10 mmol) of 8-methoxy-2-propylamino-1,2,3,4-tetrahydronaphthalene, 0.36 g (12 mmol) of paraformaldehyde and 0.1 g of copper(II) acetate monohydrate in 10 ml of dioxane at 50° C. After 5 hours at 80° C., the mixture was freed from solvent. The crude product remaining was purified by flash chromatography on silica gel using toluene/ethyl acetate gradients. 3.4 g (75%) of the title compound were obtained as a solidifying oil.

Melting point: 80°–84° C. (from ethanol) R$_f$ (toluene/ethanol 1:1): 0.51 IR (chloroform) 3008, 2967, 2949, 2839, 1740, 1589, 1470, 1440.

Example 90

2-{4-[N-(8-Methoxy-1,2,3,4-tetrahydro-2-naphthyl)-N-propylamino]but- 2-inyl}-1,2-benzisothiazol-3(2H)-one 1,1-dioxide hydrochloride By treating the compound of Example 89 with ethereal hydrochloric acid, 2.0 g of the hydrochloride were obtained as colorless crystals.

Melting point: 195°–200° C.

Example 91

8-methoxy-2-{N-propyl-N-[3-(2-isoindolinyl)propyl]}amino-1,2,3,4-tetrahydronapthalene 2.35 g of 8-methoxy-2-[N-propyl-N-(3-phthalimidoyl-propyl)]amino- 1,2,3,4-tetrahydronaphthalene in 15 ml of tetrahydrofuran were added dropwise to the suspension of 0.88 g (23 mmol) of lithium aluminum hydride in 35 ml of tetrahydrofuran at 0° C. After refluxing for 3 hours, the reaction mixture was carefully hydrolyzed using 10 ml of a 2:1 tetrahydrofuran/water mixture. 2 ml of dilute sodium hydroxide solution were subsequently added. After drying over potassium carbonate and filtration, the mixture was concentrated. The crude product obtained in this fashion is purified by flash chromatography on silica gel using toluene/ethyl acetate gradients in the presence of 2% of triethylamine. 1.0 g (46%) of the title compound were obtained as an oil.

$R_f$ (toluene/ethyl acetate 1:1): −0.1 IR (chloroform) 3010, 2938, 2840, 1585, 1470, 1439.

Example 92

8-Methoxy -2-{N-propyl-N-[3-(2-isoindolinyl)-propyl]}amino-1,2,3,4-tetrahydronaphthalene dihydrochloride It was possible to obtain the dihydrochloride in the form of pale gray crystals from the compound of Example 91 using ethereal hydrochloric acid.

Melting point: >75° C. (vitrification, decomp.)

Example 93

2-[N-(2-Methoxyethyl)-N-propyl]amino-8-methoxy-1,2,3,4-tetrahydronaphthalene

The solution of 2.0 g (6.9 mmol) of 2-(N-methoxyacetyl-N-propyl)amino- 8-methoxy-1,2,3,4-tetrahydronaphthalene in 10 ml of tetrahydrofuran was added dropwise to the boiling suspension of 0.53 g (8.3 mmol) of lithium aluminum hydride in 20 ml of tetrahydrofuran. After 2 hours at the boiling temperature, 0.5 ml of water, 0.3 ml of 20% strength sodium hydroxide solution and 1.8 ml of water were added successively to the reaction mixture. The organic phase was dried using potassium carbonate and concentrated. In this fashion, 1.5 g (79%) of the title compound were obtained as an oil.

$R_f$ (toluene:ethyl acetate 1:1): 0.36 MS: 277, 248, 232, 205, 161 IR (chloroform): 3009, 2963, 2934, 1588, 1471, 1441.

Example 94

2-[N-(2-Methoxyethyl)-N-propyl]amino-8-methoxy-1,2,3,4-tetrahydronaphthalene hydrochloride The hydrochloride was obtained as an amorphous, hygroscopic solid (1.6 g) from 1.5 g of the compound from Example 93 using ethereal hydrochloric acid.

$^1$H NMR (CD$_3$OD): δ=1.05 (t, 3H); 1.8 (m, 3H); 2.3 (m, 1H); 2.75 (m, 1H); 2.95 (m, 2H); 3.2–3.9 (m,); including 3.42 (s, 3H); 3.85 (s, 3H); 6.75 (dd, 2H); 7.15 (dd, 1H).

Example 95

8-Methoxy-2-[N-(3-phenylsulphinyl-propyl)-N-propyl]amino-1,2,3,4-tetrahydronaphthalene 1.2 g of 30% strength hydrogen peroxide were added to the solution of 3.7 g (10 mmol) of 8-methoxy-2-[N-(3-phenylthio-propyl)-N-propyl]amino-1,2,3,4-tetrahydronaphthalene in 50 ml of glacial acetic acid at 0° C. The reaction mixture was warmed to room temperature within 1 hour. 0.3 g of 30% strength hydrogen peroxide was then added, and the mixture was stirred for a further 2 hours at room temperature. The reaction mixture was poured into 10% strength potassium carbonate solution and ethyl acetate. The ethyl acetate phase was separated off, and the aqueous phase was extracted repeatedly with ethyl acetate. Drying the organic phase and concentrating gave a crude product which was purified by flash chromatography on silica gel using toluene/ethyl acetate gradients. 2.35 g (61%) of the title compound were obtained as a 1:1 diastereomeric mixture (colorless oil).

MS: 385, 368, 340, 232, 161 $^{13}$C NMR (CDCl$_3$): δ=11.8 (q), 21.1 (t), 21.9 (t), 22.0 (t), 24.9 (t), 25.0 (t), 25.8 (t), 25.9 (t), 30.0 (t), 48.2 (t), 48.6 (t), 52.1 (t), 52.1 (t), 54.8 (t), 54.9 (t), 55.1 (q), 56.1 (d), 106.7 (d), 120.7 (d), 123.9.(d), 124.9 (s), 125.9 (d), 129.0 (d), 130.7 (d), 137.6 (s), 143.9 (s), 157.4 (s).

Example 96

8-Methoxy-2-[N-(3-phenylsulphinyl-propyl)-N-propyl]amino-1,2,3,4-tetrahydronaphthalene hydrochloride It was possible to obtain the hydrochloride in the form of a colorless, hygroscopic solid from the compound of Example 95 using ethereal hydrochloric acid.

$^1$H NMR (CD$_3$OD): δ=1.05 (m, 3H); 1.8 (m, 3H); 2.2 (m, 3H); 2.6–3.9 (m) including 3.85 (2s), in total 3H; 6.85 (2d, 2H); 7.15 (dd, 1H); 7.5–7.8 (m, 5H).

Example 97

8-Methoxy-2-[N-(3-phenylsulphonylpropyl)-N-propyl]amino-1,2,3,4-tetrahydronaphthalene

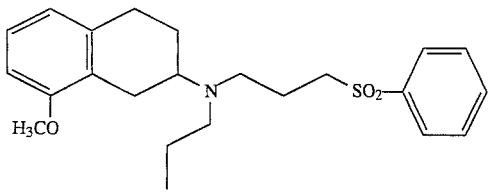

The solution of 3.7 g (10 mmol) of 2-[N-(3-phenylthiopropyl)-N-propyl]amino- 8-methoxy-1,2,3,4-tetrahydronaphthalene and 2.6 g of 30% strength hydrogen peroxide in 50 ml of glacial acetic acid was heated for 1 hour at 90° C. 0.4 g of 30% strength hydrogen peroxide were then added. After a further hour at 90° C., 0.4 g of 30% strength hydrogen peroxide were added. After a further 2 hours at 90° C., the mixture was cooled. The reaction mixture was poured into approximately 10% strength potassium carbonate solution and ethyl acetate. The ethyl acetate phase was separated off, and the aqueous phase was extracted. Drying and concentrating gave a crude product, which was purified by flash chromatography on silica gel using toluene/ethyl acetate gradients. In this fashion, 1.65 g (41%) of the title compound were obtained as a viscous syrup.

$R_f$ (toluene/ethyl acetate 3:1): 0.23 MS: 401, 372, 232, 161

Example 98

8-Methoxy-2-[N-(3-phenylsulphonylpropyl)-N-propyl]amino-1,2,3,4-tetrahydronaphthalene hydrochloride It was possible to obtain the hydrochloride in the form of a colorless, very hygroscopic solid from the compound of Example 97 using ethereal hydrochloric acid.

$^1$H NMR (CD$_3$OD): δ=1.05 (t, 3H); 1.8–2.0 (m, 3H); 2.1–2.4 (m, 3H); 2.7–3.9 (m, including 3.85 (s, 3H); 6.75 (2d, 2H); 7.15 (t, 1H); 7.6–7.8 (m, 3H); 8.0 (d, 2H).

Example 99

2-[N-3-(4,4-Dimethyl-2,6-dioxo-piperidin-1-yl)propyl-N-propyl]amino- 8-methoxy-1,2,3,4-tetrahydronaphthalene

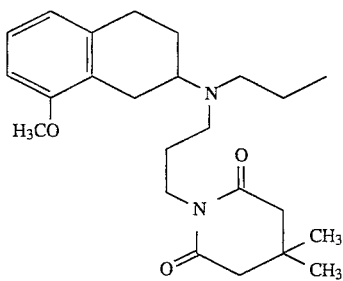

2.2 g (8 mmol) of 2-[N-(3-aminopropyl)-N-propyl]amino-8-methoxy-1,2,3,4-tetrahydronaphthalene, 1.1 g (8 mmol) of 3,3-dimethylglutaric anhydride, 1 drop of tributylamine and 0.5 g of 3 Å molecular sieve were refluxed for 2 hours in 5 ml of toluene. The crude product obtained after filtration and concentration was purified by flash chromatography on silica gel using toluene/ethyl acetate in toluene/ethanol gradients. 1.6 g (50%) of the title compound were obtained as a viscous syrup.

$R_f$ (toluene/methanol 4:1): 0.3 MS 400, 371, 232, 182, 161 IR (chloroform) 3007, 2965, 2875, 2841, 1727, 1670, 1602, 1588, 1471, 1441.

Example 100

2-[N-3-(4,4-Dimethyl-2,6-dioxo-piperidin-1-yl)propyl-N-propyl]amino- 8-methoxy-1,2,3,4-tetrahydronaphthalene hydrochloride It was possible to obtain the hydrochloride from Example 99 using ethereal hydrochloric acid.

The following were prepared analogously to Examples 98 and 99:

Example 101

2-[N-2-(4,4-Dimethyl-2,6-dioxo-piperidin-1-yl)ethyl-N-propyl]amino- 8-methoxy-1,2,3,4-tetrahydronaphthalene

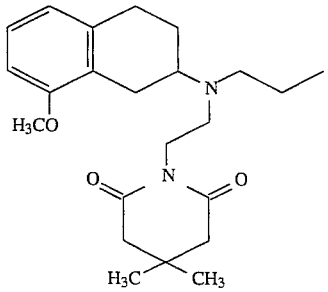

Yield: 2.3 g (75%) of the title compound as a viscous syrup. $R_f$ (toluene/methanol 4:1): 0.49 IR (chloroform) 3009, 2966, 2933, 2877, 1726, 1675, 1603, 1587, 1470, 1441.

Example 102

2-[N-2-(4,4-Dimethyl-2,6-dioxo-piperidin-1-yl)ethyl-N-propyl]amino- 8-methoxy-1,2,3,4-tetrahydronaphthalene hydrochloride It was possible to obtain the hydrochloride from the compound of Example 101 using ethereal hydrochloric acid.

The following were prepared analogously to Examples 1–12:

Example 103

8-(8-Methoxy-1,2,3,4-tetrahydro-2-naphthalenyl)-1-phenyl-1,3,8-triazabicyclo[4,5]decan-4-one

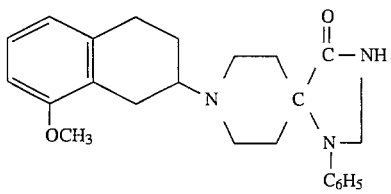

Melting point (from toluene/petroleum ether): 210°–220° C. IR (KBr): 3424, 2926, 2839, 1703, 1600, 1502, 1470.

Example 104

2-{N-[3-(1,2,3,4-Tetrahydronaphthalen-1-yloxy)-propyl]}amino- 8-methoxy-1,2,3,4-tetrahydronaphthalene (diastereomeric mixture)

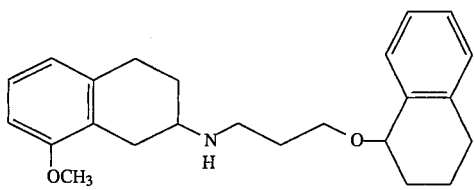

From 8-methoxy-2-tetralone and 1-(3-aminopropyloxy)-1,2,3,4-tetrahydronaphthalene (producible from 1-hydroxy-1,2,3,4-tetrahydronaphthalene and acrylonitrile with subsequent reduction).

$R_f$ (acetonitrile:triethylamine 30:1): 0.44

Example 105

8-Methoxy-2-{3-[3-(N-4-methylphenylsulphonyl)indolyl]propyl}amino- 1,2,3,4-tetrahydronaphthalene

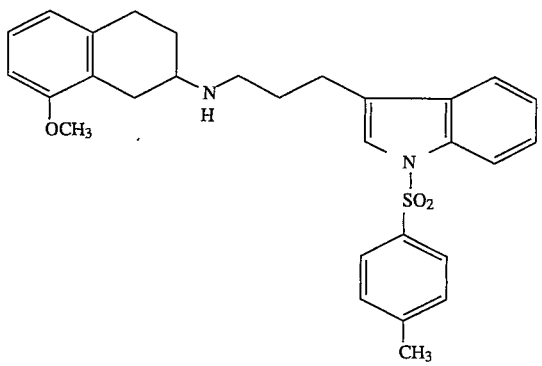

From 8-methoxy-2-tetralone and 3-(3-aminopropyl)-1-tosylindole $R_f$ (chloroform:methanol 2:1): 0.5

The following were prepared analogously to Examples 17–24:

Example 106

8-Methoxy-2-{N-propyl-N-{3-[3-(N-4-methylphenylsulphonyl)indolyl]propyl}}amino- 1,2,3,4-tetrahydronaphthalene

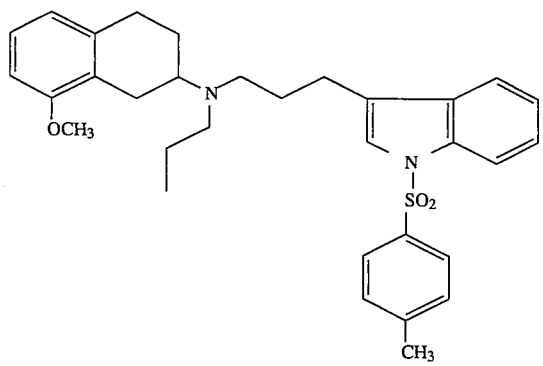

$R_f$ (toluene:ethyl acetate 1:1): 0.34 IR (chloroform): 3006, 2936, 2839, 1599, 1586, 1495.

Example 107

8-Methoxy-2-{N-propyl-N-{3-[3-(N-4-methylphenylsulphonyl)indolyl]propyl}}amino- 1,2,3,4-tetrahydronaphthalene hydrochloride Melting point: 55°–90° C. (with decomposition) $^1$H NMR (CD$_3$OD): δ=0.9–1.0 (m, 3H); 1.6–1.9 (m, 4H); 2.1–2.2 (m, 3H); 2.3 (s, 3H); 2.6–3.3 (m); 3.6–3.8 (m, 1H); 3.8 (s, 3H); 6.7 (d, 1H); 6.75 (d, 1H); 7.15 (dd, 1H); 7.25 (m, 3H); 7.35 (dd, 1H); 7.55 (m, 2H); 7.8 (m, 2H); 8.0 (d, 1H).

The following were prepared analogously to Examples 25–34:

Example 108

2-{3-[6-(1,2,3-Benzothiadiazolyl)oxy]ethyl-N-propyl}amino- 8-methoxy-1,2,3,4-tetrahydronaphthalene

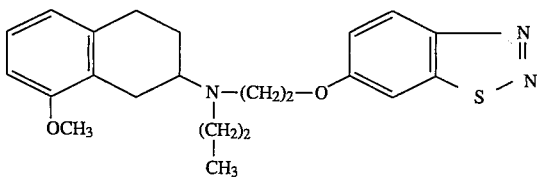

From 2-propylamino-8-methoxy-1,2,3,4-tetrahydronaphthalene and 6-(2-chloroethyloxy)-1,2,3-benzothiadiazole.

$R_f$ (toluene:ethyl acetate 3:1): 0.46 MS: 397, 368, 232, 161

The following were prepared analogously to Examples 45–54:

Example 109

2-{N-[3-(4-Fluorophenylsulphonamido)ethyl]-N-propyl}amino-8-methoxy-1,2,3,4-tetrahydronaphthalene hydrochloride

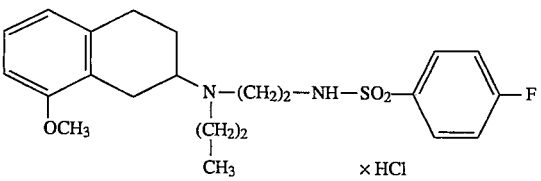

Melting range: 95°–110° C. $^1$H NMR (CD$_3$OD): δ=1.05 (t, 3H); 1.7–2.0 (m, 2H); 2.35 (m, 1H); 2.75 (dd, 1H); 2.95 (m, 2H); 3.2–3.6 (m); 3.85 (s, 3H); 6.75 (d, 1H); 6.8 (d, 1H); 7.15 (dd, 1H); 7.35 (m, 2H); 7.95 (m, 2H) ppm.

Example 110

2-{N-[3-(4-Methylphenylsulphonylamido)methyl]phenylmethyl-N-propyl}- 8-methoxy-1,2,3,4-tetrahydronaphthalene

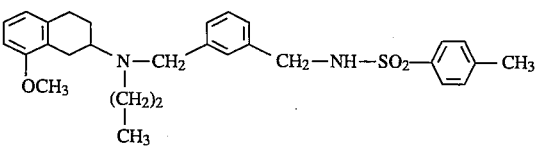

$R_f$ (toluene:ethyl acetate 3:1): 0.42

Example 111

2-{N-[3-(4-Methylphenylsulphonylamido)methyl]phenyl-methyl-N-propyl}- 8-methoxy-1,2,3,4-tetrahydronaphthalene hydrochloride Melting point: 115° C.

Example 112

2-{N-[2-(4-Methylphenylsulphonylamido)methyl]phenyl-methyl-N-propyl}- 8-methoxy-1,2,3,4-tetrahydronaphthalene

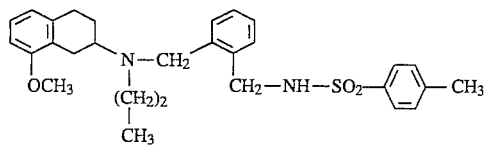

$R_f$ (toluene:ethyl acetate 3:1): 0.73

Example 113

2-{N-[2-(4-Methylphenylsulphonylamido)methyl]phenyl-methyl-N-propyl}- 8-methoxy-1,2,3,4-tetrahydronaphthalene hydrochloride Melting point: 120° C.

Example 114

2-{N-[4-(4-Methylphenylsulphonylamido)methyl]phenyl-methyl-N-propyl}- 8-methoxy-1,2,3,4-tetrahydronaphthalene

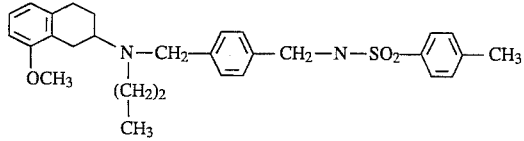

$R_f$ (toluene:ethyl acetate 3:1): 0.37

Example 115

2-{N-[4-(4-Methylphenylsulphonylamido)methyl]phenyl-methyl-N-propyl}- 8-methoxy-1,2,3,4-tetrahydronaphthalene hydrochloride Melting point: 185° C.

The following were prepared analogously to Examples 99–102:

Example 116

2-[N-2-(3-Phenyl-2,6-dioxo-piperidin-1-yl)ethyl-N-propyl]amino- 8-methoxy-1,2,3,4-tetrahydronaphthalene

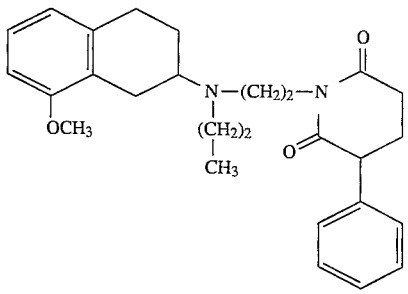

From the compound of Example 36 and 2-phenylglutaric anhydride.

Yield: 77% of a viscous syrup $R_f$ (methylene chloride:methanol 10:1): 0.9 IR (chloroform): 3010, 2963, 2841, 1727, 1676, 1602, 1587.

Example 117

2-[N-2-(3-Phenyl-2,6-dioxo-piperidin-1-yl)ethyl-N-propyl]amino- 8-methoxy-1,2,3,4-tetrahydronaphthalene hydrochloride Melting range: 110°–115° C.

Example 118

2-[N-(2-Ethoxycarbonylamido-propyl)-N-propyl]amino-8-methoxy-1,2,3,4-tetrahydronaphthalene

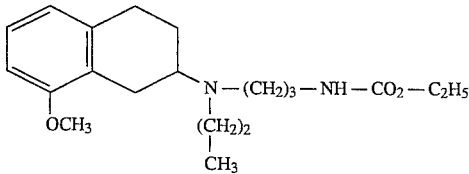

A solution of 220 mg (2.0 mmol) of ethyl chloroformate in 2 ml diisopropyl ether was added dropwise to a solution 550 mg (2.0 mmol) of the compound from Example 35 and 1.40 g (20 mmol) of powdered potassium carbonate in 10 ml of diisopropyl ether at 0° C. After 2 hours, the mixture was brought to room temperature and stirred for 3 days. The reaction mixture was poured into 50 ml of ethyl acetate/ice water mixture. The aqueous phase was extracted repeatedly with ethyl acetate. Drying (magnesium sulphate) and concentrating the combined organic extracts gave a crude product, which was purified by chromatography on a silica gel (toluene/ethyl acetate or toluene/ethanol gradients). This gave 380 mg (55%) of the title compound as a viscous oil.

MS: 348, 319, 232, 161 IR (chloroform): 3008, 2937, 2855, 1704, 1588, 1512, 1471.

Example 119

2-[N-(2-Ethoxycarbonylamido-propyl)-N-propyl]amino-8-methoxy-1,2,3,4-tetrahydronaphthalene hydrochloride It is possible to obtain the hydrochloride in ethereal solution as a hygroscopic foam from the compound of Example 118 using ethereal hydrochloric acid.

¹H NMR (CD₃OD): Δ=1.05 (t, 3H); 1.25 (t, 3H); 1.7–2.1 (m, 5H); 2.3 (m, 1H); 2.6–3.5 (m); 3.7–3.9 (m, 4H), including 3.85 (s, 3H); 4.10 (q, 2H); 6.75 (m, 2H); 7.15 (dd, 1H) ppm.

Example 120

2-[N-(1-Adamantylcarboxamido-ethyl)-N-propyl]amino-8-methoxy-1,2,3,4-tetrahydronaphthalene

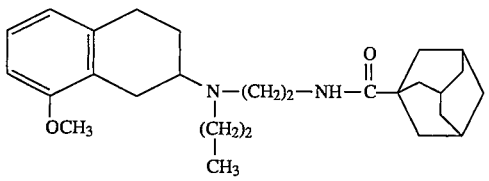

A solution of 0.80 g (4.0 mmol) of 1-adamantanecarbonyl chloride in 5 ml of toluene was added to the solution of 1.05 g (4.0 mmol) of the compound from Example 36 in 10 ml of toluene at 0° C. The mixture was allowed to come to room temperature and was stirred for 1 day. Sodium hydrogen carbonate was added to the solution, and the mixture was extracted. Drying the organic phase (magnesium sulphate) and concentrating gave 1.80 g of crude product. From this, 1.50 g of the title compound (88%) were obtained as a syrup by flash chromatography on silica gel (toluene/ethyl acetate or toluene/ethanol gradients).

IR (chloroform): 3407, 3005, 2908, 2856, 1638, 1588, 1509, 1471 R_f (toluene:ethanol 3:1): 0.65.

Example 121

2-[N-(1-Adamantylcarboxamido-ethyl)-N-propyl]amino-8-methoxy- 1,2,3,4-tetrahydronaphthalene hydrochloride The hydrochloride was obtained from this as an amorphous solid in ethereal solution using ethereal hydrochloric acid.

¹H NMR (CD₃OD): δ=1.1 (t, 3H); 1.6–2.1 (m), 2.3 (m, 1H); 2.7 (m, 1H); 2.95 (m, 2H); 3.1–3.9 (m); 6.7 (d, 1H); 6.75 (d, 1H); 7.15 (dd, 1H) ppm.

Example 122

2-[N-(1-Adamantylcarboxamido-propyl)-N-propyl]amino-8-methoxy-1,2,3,4-tetrahydronaphthalene

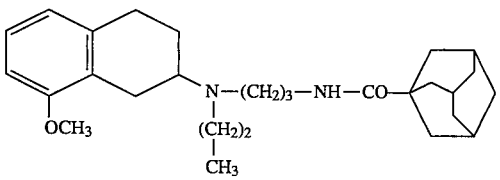

Analogously to Example 120 using the compound from Example 35.

R_f (toluene:ethanol 3:1): 0.53 IR (methylene chloride): 3467, 3318, 3004, 2910, 2856, 1630, 1588, 1510, 1470.

Example 123

2-[N-(1-Adamantylcarboxamido-propyl)-N-propyl]amino-8-methoxy- 1,2,3,4-tetrahydronaphthalene hydrochloride ¹H NMR (CD₃OD): δ=1.05 (t, 3H); 1.55–2.1 (m); 2.35 (m, 1H); 2.30 (m, 1H); 2.95 (m, 2H); 3.1–3.4 (m); 3.75 (m, 1H); 3.85 (s, 3H); 6.70 (d, 1H); 6.75 (d, 1H); 7.15 (t, 1H) ppm.

Example 124

8-Methoxy-2-[N-propyl-N-(2-triphenylmethylaminoethyl)]-amino-1,2,3,4-tetrahydronaphthalene

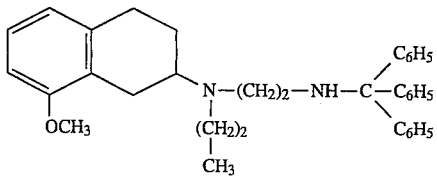

1.70 g (6.0 mmol) of trityl chloride were added to the solution of 1.30 g (5.0 mol) of the compound from Example 36 and 0.75 g (7.5 mmol) of triethylamine in 30 ml of methylene chloride at 0° C. The mixture was subsequently brought to reaction for 15 hours at room temperature. Water was added to the reaction mixture, which was extracted thoroughly. The organic phase was dried (magnesium sulphate) and concentrated. It was possible to purify the crude product obtained in this fashion by chromatography on silica gel (toluene/ethyl acetate gradients). In this fashion, 2.05 g (81%) of the title compound were obtained as a syrup.

R_f (toluene/ethyl acetate 3:1): 0.67 IR (chloroform): 3586, 3306, 3062, 3006, 2961, 2839, 1586, 1489, 1470.

Example 125

8-Methoxy-2-[N-propyl-N-(2-triphenylmethylaminoethyl)]amino- 1,2,3,4-tetrahydronaphthalene dihydrochloride Obtained from the ethereal solution using ethereal hydrochloric acid.

Melting point: 140°–150° C. Analysis (C₃₅H₄₀N₂O× 2HCl×H₂O): Calc.: C 70.6 H 7.4 N 4.7 O 5.4 Cl 11.9 Found: C 70.8 H 7.7 N 4.7 O 5.0 Cl 12.2

Example 126

8-Methoxy-2-[N-propyl-N-(2-triphenylmethyl)aminopropyl)]amino-1,2,3,4-tetrahydronaphthalene

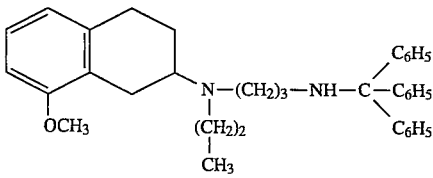

As in Example 124 using the compound from Example 35.

R_f (toluene:ethyl acetate 3:1): 0.40 IR (chloroform): 3584, 3061, 3008, 2961, 2839, 1587, 1489, 1470.

Example 127

8-Methoxy-2-[N-propyl-N-(2-triphenylmethyl)aminopropyl)]amino- 1,2,3,4-tetrahydronaphthalene dihydrochloride The product is precipitated in the form of colorless crystals from the compound of Example 126 using ethereal hydrochloric acid.

Melting range: 130° C.–150° C.

USE EXAMPLES

Example 128

A.) Affinity to the 5-HT₁ receptor

In Table 1, as an example, the high affinity of the compounds according to the invention to 5-hydroxytryptamine receptors of the sub-type 1 is shown. The values specified are data which were determined from receptor binding studies using calf hippocampus membrane preparations. 3H-serotonin was used for this purpose as radioactively labelled ligand.

TABLE 1

| Compound of Example No. | Ki (nmol/l) |
| --- | --- |
| 20 | 11 |
| 22 | 3 |
| 26 | 2 |
| 34 | 1 |
| 42 | 4 |
| 45 | 1 |
| 58 | 4 |
| 62 | 4 |

B.) Investigation of the serotonin-agonistic/antagonistic action.

To this purpose, the action on the contraction, caused by serotonin, of the arteria basilaris of the dog is investigated [cf. Peroutka et al., Brain Research 259, 327 (1983)].

TABLE 2

| Compound of Example No. | Effect | |
| --- | --- | --- |
|  | agonistic | antagonistic |
| 2 | + | + |
| 22 | ++ | 0 |
| 34 | 0 | ++ |
| 45 | 0 | +++ |
| 66 | + | ++ |
| For comparison from EP-Al 41 488 $R^1 = H, R^2 = nC_3H_7, R^3 = nC_3H_7$ | ++ | 0 |

In this test model, an agonistic action can be detected by the serotonin-mimetic action (contraction). The agonistic active component shows itself by the dosage-dependent suppression of the contraction during the administration of serotonin to preparations pre-treated with the test substance.

Example 129

Abolition of the defensive behavior of the mouse

In this test (Tedeschi et al., J. Pharm. Esep. Ther. 125, 28 to 34 (1959)), the tranquilizing and anxiolytic effect of active compounds is investigated. In this test, the fighting activity of mice which have been kept isolated for at least 8 days is measured after stimulation with electrical shocks to the feet with and without administration of the substituted basic 2-aminotetralins according to the invention. The 2-aminotetralins inhibit the fighting activity of the mice.

It will be understood that the specification and examples are illustrative but not limitative of the present invention and that other embodiments within the spirit and scope of the invention will suggest themselves to those skilled in the art.

We claim:

1. The compound 2-[N-ethoxycarbonylamidopropyl)-N-propyl]amino-8-methoxy-1,2,3,4-tetrahydronaphthalene of the formula

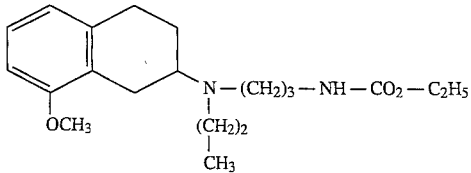

or its hydrochloride salt.

* * * * *